(12) United States Patent
Barberio

(10) Patent No.: US 7,250,034 B2
(45) Date of Patent: Jul. 31, 2007

(54) VENTING DEVICES FOR SURGICAL CASTS AND OTHER ORTHOPEDIC DEVICES

(76) Inventor: Alessandro Barberio, 4325 Steeles Avenue, Suite 205, Toronto, Ontario (CA) M3N 1V7

( * ) Notice: Subject to any disclaimer, the term of this patent is extended or adjusted under 35 U.S.C. 154(b) by 588 days.

(21) Appl. No.: 10/436,566

(22) Filed: May 13, 2003

(65) Prior Publication Data
US 2004/0230148 A1 Nov. 18, 2004

(51) Int. Cl.
*A61F 5/00* (2006.01)
(52) U.S. Cl. ............................................. 602/14; 602/3
(58) Field of Classification Search .................... 602/5, 602/6, 7–12, 14, 54, 56–58, 1–4, 13, 60, 602/44, 78, 20–22; 128/DIG. 20; 601/11, 601/15, 16, 17, 148
See application file for complete search history.

(56) References Cited

U.S. PATENT DOCUMENTS

| | | | | |
|---|---|---|---|---|
| 432,899 | A * | 7/1890 | Reenstierna | 602/6 |
| 1,213,941 | A * | 1/1917 | Patrick | 36/3 A |
| 2,666,207 | A | 1/1954 | Lucas | |
| 2,704,067 | A | 3/1955 | Moses | |
| 2,731,963 | A | 1/1956 | Blank | |
| 2,837,088 | A * | 6/1958 | Moses | 602/14 |
| 3,097,644 | A * | 7/1963 | Parker | 602/79 |
| 3,307,537 | A | 3/1967 | Simon et al. | |
| 3,415,243 | A * | 12/1968 | Sheldon | 602/8 |
| 3,656,475 | A * | 4/1972 | Hanrahan, Jr. | 602/8 |
| 3,656,477 | A * | 4/1972 | Thomas et al. | 602/14 |
| 3,701,349 | A | 10/1972 | Larson | |
| 3,850,167 | A * | 11/1974 | Seeley | 602/6 |
| 3,935,355 | A * | 1/1976 | Kuhn | 403/267 |
| 3,998,220 | A * | 12/1976 | Cleer et al. | 602/14 |
| 4,019,506 | A * | 4/1977 | Eschmann | 602/8 |
| 4,306,549 | A * | 12/1981 | Canie | 602/8 |

(Continued)

FOREIGN PATENT DOCUMENTS

CA 2254492 11/1998

OTHER PUBLICATIONS

Barberio, Surgical Cast Venting Device, 2,254,492.*

(Continued)

*Primary Examiner*—Patricia Bianco
*Assistant Examiner*—Huong Q. Pham
(74) *Attorney, Agent, or Firm*—Young & Basile, PC

(57) ABSTRACT

A surgical cast venting device comprises two elongate strips or two layers of flexible material, at least one of which is porous. The strips or layers are spaced apart from each other and extend parallel to each other. Flexible, solid spacer members are arranged between the two strips or layers and connect them together. These members form air passageways between adjacent spacers so that air is normally free to pass along the passageways. A moisture-absorbent fabric layer extends along an outer side of the porous strip or layer opposite the spacers. In an alternate version, there is a first strip which is porous and a series of substantially flat, flexible outer members arranged in a row from one end of the strip to an opposite end. The outer members are spaced from the strip and opposite side edges of the strip and of the outer members are aligned with one another.

20 Claims, 14 Drawing Sheets

U.S. PATENT DOCUMENTS

| | | | |
|---|---|---|---|
| 4,308,862 A * | 1/1982 | Kalmar | 602/14 |
| 4,387,710 A * | 6/1983 | Beatty, III | 602/14 |
| 4,483,332 A * | 11/1984 | Rind | 602/8 |
| 4,554,317 A | 11/1985 | Behar et al. | |
| 4,898,160 A * | 2/1990 | Brownlee | 602/14 |
| 4,928,678 A * | 5/1990 | Grim | 602/8 |
| 4,945,903 A * | 8/1990 | Alper | 602/5 |
| 5,014,363 A * | 5/1991 | Hubner et al. | 2/243.1 |
| 5,277,954 A * | 1/1994 | Carpenter et al. | 428/71 |
| 5,415,622 A * | 5/1995 | Kelley | 602/5 |
| 5,468,219 A | 11/1995 | Crippen | |
| 5,474,525 A * | 12/1995 | Blott | 602/63 |
| 5,511,323 A | 4/1996 | Dahlgren | |
| 5,514,080 A * | 5/1996 | Blott et al. | 602/5 |
| 5,527,265 A * | 6/1996 | McKeel | 602/6 |
| 5,540,964 A * | 7/1996 | Mallen | 428/36.1 |
| 5,637,077 A * | 6/1997 | Parker | 602/8 |
| 5,643,183 A * | 7/1997 | Hill | 602/3 |
| 5,755,678 A * | 5/1998 | Parker et al. | 602/6 |
| 5,916,184 A * | 6/1999 | McKeel | 602/6 |
| 6,022,331 A * | 2/2000 | Darcey | 602/12 |
| 6,053,882 A * | 4/2000 | Johansen | 602/14 |
| 6,511,927 B1 * | 1/2003 | Ellis et al. | 442/77 |
| 6,547,751 B1 * | 4/2003 | Barberio | 602/14 |
| 6,616,622 B1 * | 9/2003 | Barberio | 602/14 |

OTHER PUBLICATIONS

Gore Cast Liner by W-L Gore & Associates dated Apr. 1996 (2 pages).

* cited by examiner

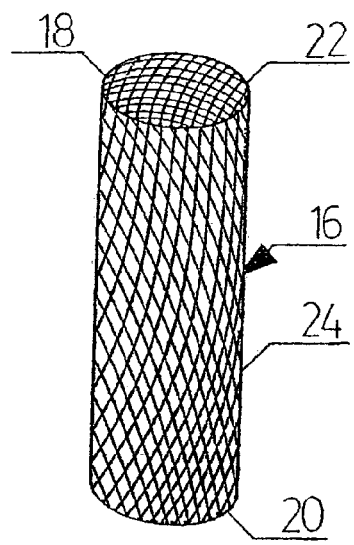
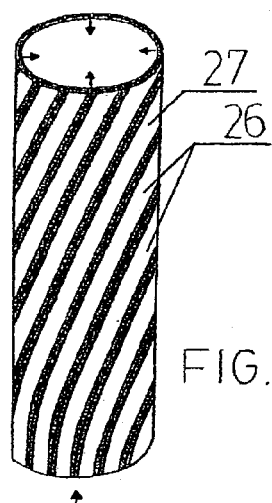
FIG. 3
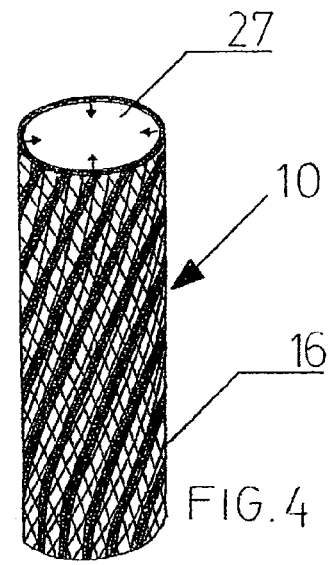
FIG. 4
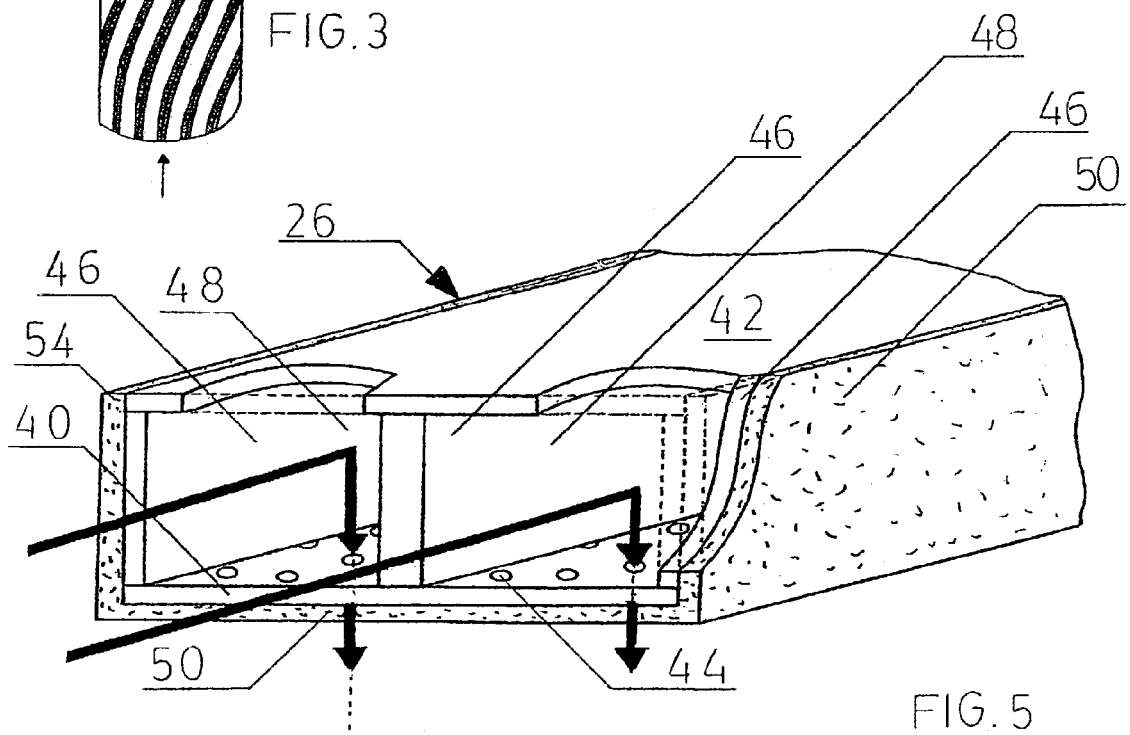
FIG. 5

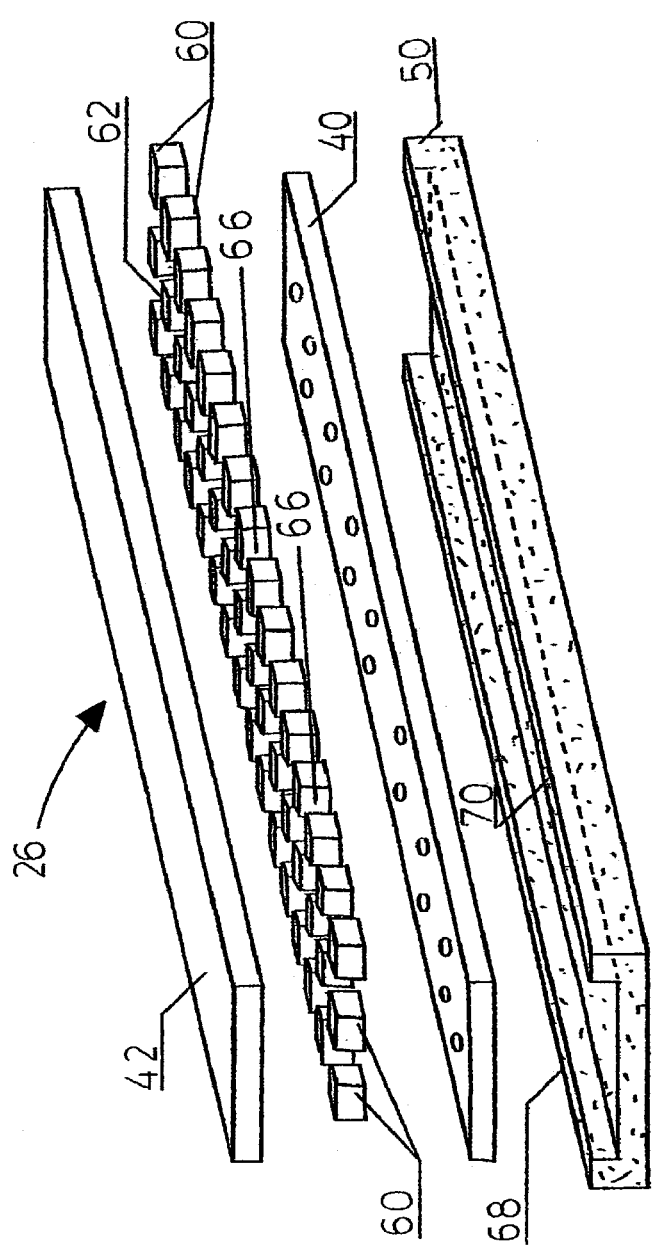
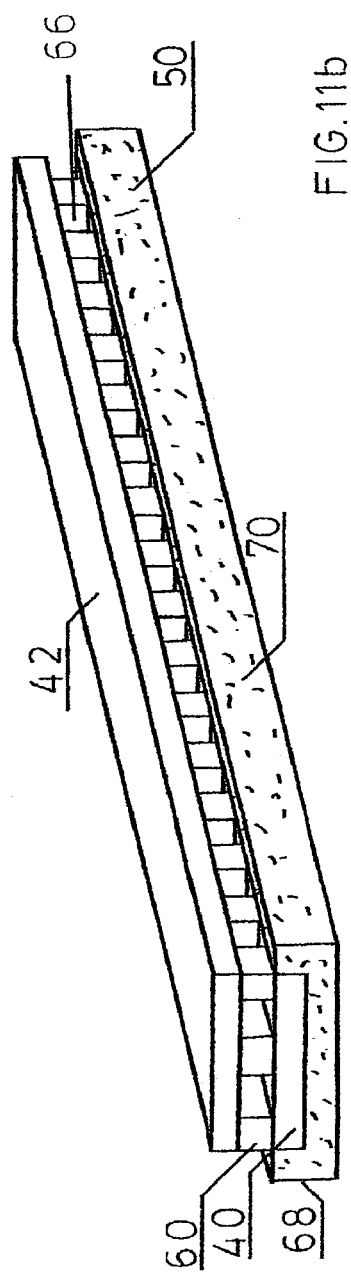
FIG.11a
FIG.11b

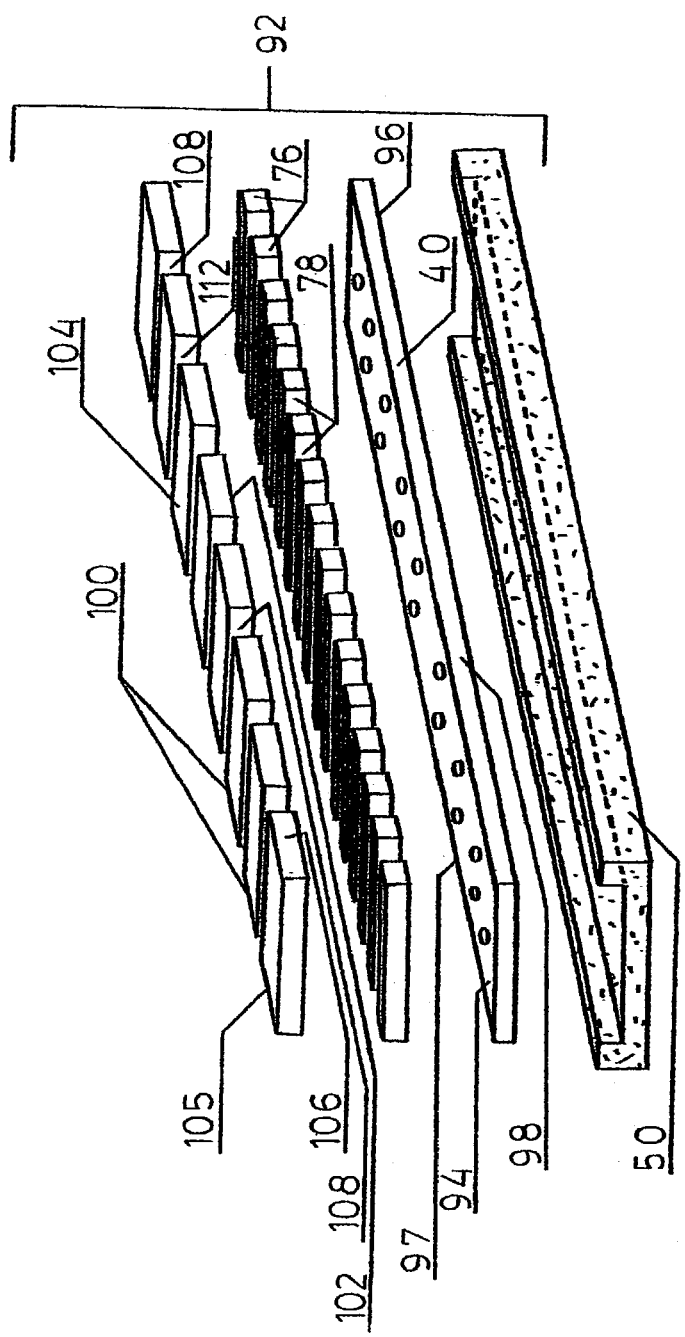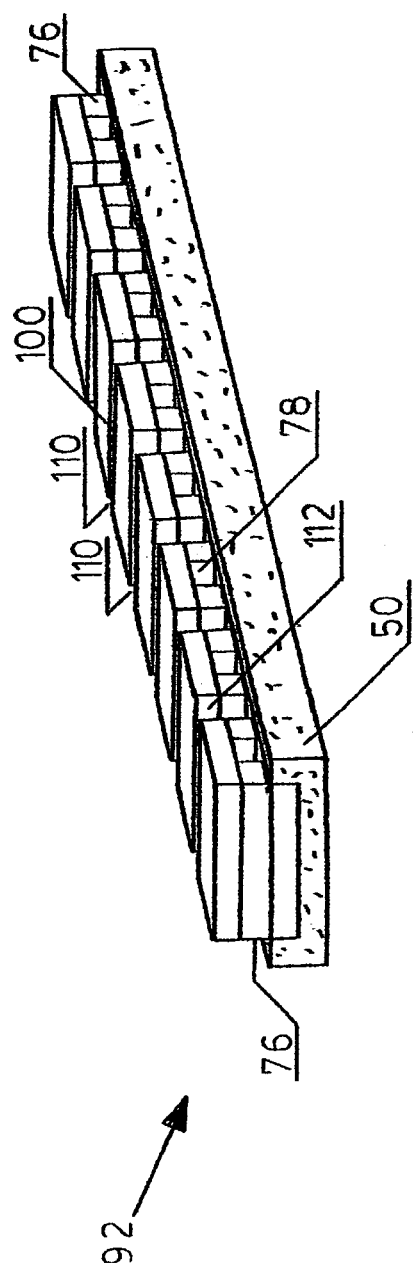

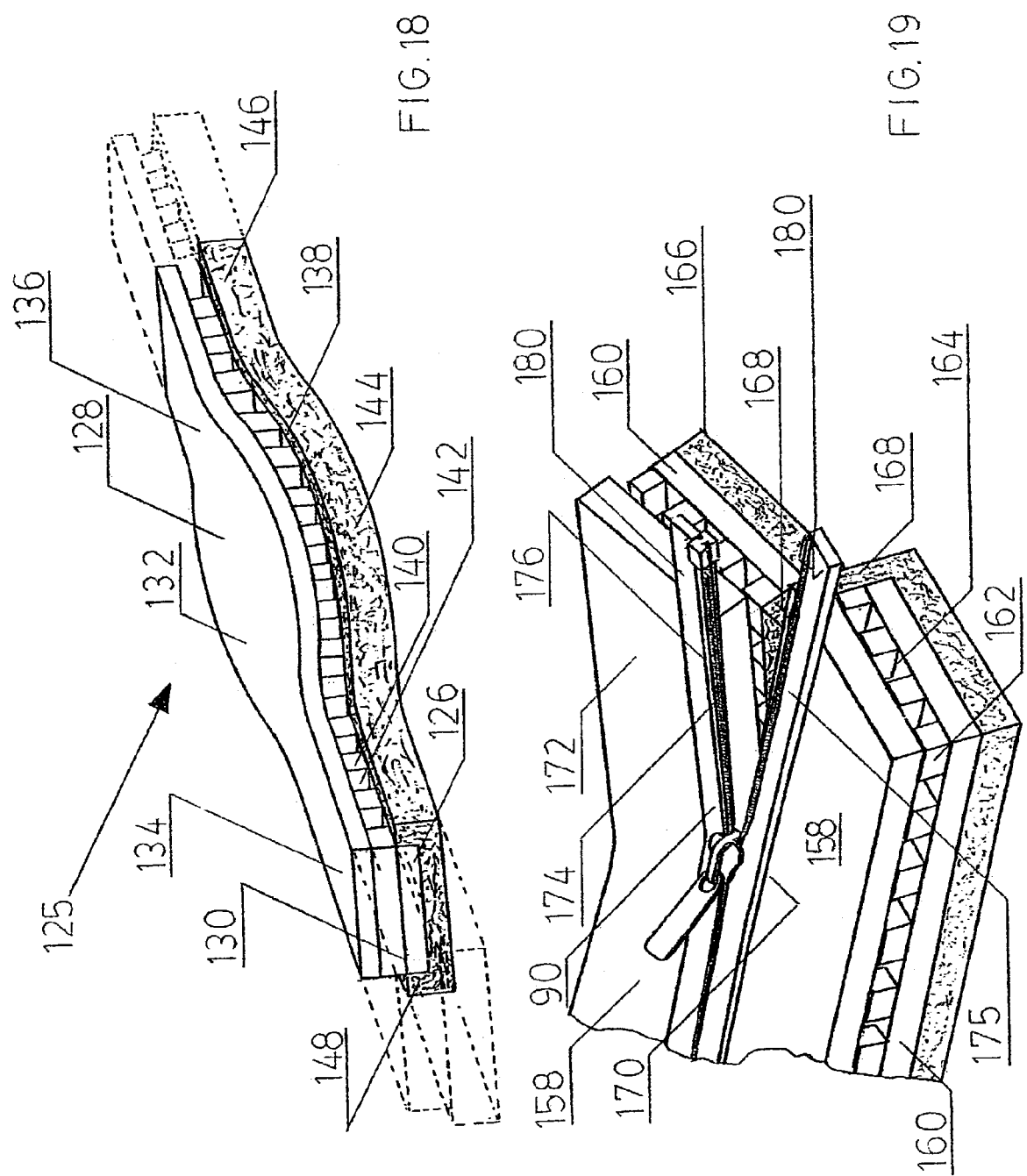

VENTING DEVICES FOR SURGICAL CASTS AND OTHER ORTHOPEDIC DEVICES

BACKGROUND OF THE INVENTION

This invention relates to venting devices for surgical casts and medical devices such as braces and splints and, in particular, to devices for circulating air under a rigid cast, brace, or splint that may be applied, for example, to permit healing of a broken bone.

A variety of devices for venting surgical casts have been proposed in the past but generally speaking these devices have not met with commercial success to date. Generally, these devices may have tubes which form air passageways to permit air circulation between the rigid cast exterior and the patient's skin. One such venting device is taught in recent U.S. Pat. No. 4,898,160 which issued Feb. 6, 1990 to Alliance Group Inc. This device includes a multiple channeled, flexible form that is placed adjacent to the skin and that is able to adapt to the contour of the body part. The sloping walls of the channels can be formed with a plurality of spaced-apart apertures. Extending upwardly from an upper layer of this device are a number of tubular vents which can extend through the conventional cast material. An air supply line can be connected to the vent opening so as to allow air under pressure to flow into the air passageways. This known venting device can be placed initially over a cast stockingette which is normally first placed on the body part.

In applicant's own U.S. patent application Ser. No. 09/533,214 filed Mar. 23, 2000, there are described a number of different versions of devices for venting surgical casts. In one preferred embodiment, the venting device includes an elongate porous woven fabric strip to which are attached a plurality of flexible, elongate tubes with holes distributed along their respective lengths. The tubes are distributed along the length of the fabric strip and on one side thereof. The elongate strip is suitable for winding around part of a human's body or an animal's body prior to application of a surgical cast. Preferably, the fabric strip comprises a cotton gauze material. Instead of tubes for aerating devices, the aerating devices can take a variety of other forms including flexible layers of interconnected non-woven plastic threads which form numerous, small air passageways, a plurality of spiral-shaped resilient plastic members distributed over the fabric strip, and a plurality of corrugated plastic members, each of which is perforated with numerous small holes.

Experiments conducted by the applicant on various forms of venting devices have shown that key factors in their potential success include their ease of use by medical practitioners, including doctors and nurses, and the amount of comfort that is provided by the venting device after it has been applied and is in position below a rigid cast. Tests conducted by the applicant have shown that it is highly desirable that the venting device be constructed in a way which will apply an even amount of pressure on the skin of the user and in a way which will not cause pinching of the user's skin if the venting device is properly applied. Other significant factors include the ability of the venting device to fit closely on the limb to which it is being applied and in a manner which will not create pressure points on the skin and other regions of discomfort.

Accordingly, it is an object of the present invention to provide an improved venting device which will not cause undue comfort to the wearer or patient when used under a rigid cast, brace, or similar orthopedic device and which can be made at a reasonable cost.

It is a further object of the present invention to provide an improved venting device for a cast, brace, or similar orthopedic device, this venting device including at least one elongate strip of flexible material that is porous to allow passage of air to the skin of the user and also flexible spacer members that are connected to the at least one strip and that form air passageways between the spacer members whereby air can normally pass along these passageways so as to permit air circulation substantially across the length and width of the venting device.

SUMMARY OF THE INVENTION

According to one aspect of the invention, a venting device for use under a surgical cast or other orthopedic device has a length, a width and opposite side edges and includes two elongate strips of flexible material, the material of one of these strips being porous. The strips are spaced apart from each other and extend substantially parallel to each other, both lengthwise and widthwise. The strips have inner sides which face each other and opposite outer sides. Flexible, solid spacer members are arranged between the two strips and connect the two strips together. These spacer members form air passageways between adjacent spacer members so that air is normally free to pass along the passageways so as to permit air circulation substantially across the length and width of the venting device. A moisture-absorbent, porous fabric layer extends in a longitudinal direction along the outer side of the porous strip. This fabric layer covers the outer side and is attached to the porous strip. The fabric layer at least partially covers the opposite side edges of the venting device that extend between the outer sides of the two elongate strips.

Preferably the porous strip has numerous holes distributed evenly over its outer side, these holes extending through the strip to its inner side. Preferably, the porous strip, at least, is made of ethyl vinyl acetate (EVA) or NYPLEX® (nitrile and PVC) or PLASTAZOTE™.

According to another aspect of the invention, a venting apparatus for a surgical cast, brace, splint or similar orthopedic device is provided and has a porous, flexible tube material having at least some elasticity, this tube having two opposite ends which are open and inner and outer surfaces. A plurality of the aforementioned venting devices are attached to the inner surface of this tube and each is arranged in a side edge to side edge manner relative to adjacent venting devices. The venting devices extend in a spiral shape around a central axis of the tube. The porous strip of each venting device faces radially inwardly. The venting apparatus is adapted for placement around part of the human body or animal body prior to application of the surgical cast, brace, splint, or other orthopedic device over this part of the body.

In one preferred embodiment, the flexible tube is made of SURGILAST® net.

Further features and advantages will become apparent from the following detailed description taken in conjunction with the accompanying drawings.

BRIEF DESCRIPTION OF THE DRAWINGS

FIG. 3 is an isometric view showing the major components of a venting apparatus separate from one another for illustrative purposes;

FIG. 4 is an isometric view of the major components of FIG. 3 after they have been combined in a telescoping manner;

FIG. 5 is an isometric, schematic illustration of a simple form of venting device constructed in accordance with the invention, with portions broken away for purposes of illustration;

FIG. 11a is an isometric detail view illustrating a venting device like that shown in FIG. 8, but showing this device in a longer, strip form with its components separated for sake of illustration;

FIG. 11b is an isometric view of the venting device of FIG. 11a but with the components assembled and attached to one another;

FIG. 15 is an isometric detail view of yet another form of venting device of the invention, again with the components separated from each other;

FIG. 16 is an isometric view of the venting device of FIG. 15 but showing the components connected together;

FIG. 18 is a perspective view of another embodiment of venting device, this view showing the top layer of the venting device and one long side edge thereof;

FIG. 19 is an isometric detail view illustrating a zipper fastener attached to side edges of a venting device constructed in accordance with the invention with only edge sections of the venting device being shown;

DETAILED DESCRIPTION OF PREFERRED EMBODIMENT

Figure 1:
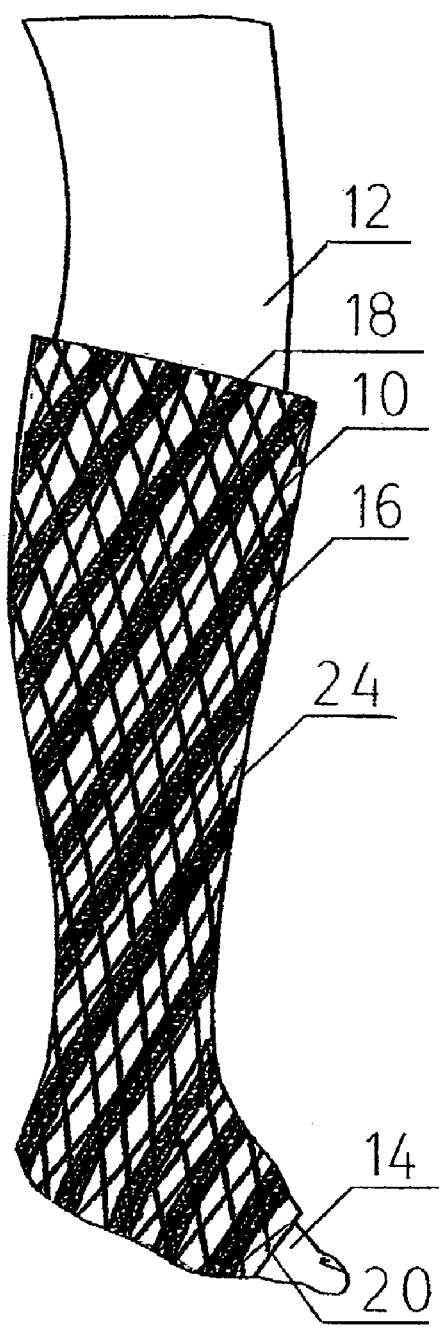
FIG. 1 is a schematic side illustration of a venting device constructed in accordance with the invention applied to a person's leg and foot.

Illustrated in FIG. 1 is one version of a venting apparatus 10 constructed in accordance with the invention. The apparatus 10 is shown applied around the lower section of a human leg 12 and a foot 14. The preferred apparatus includes a porous, flexible tube 16 of material having at least some elasticity and preferably in the form of a net structure. This tube can be seen most clearly in FIG. 3 where it is shown separately from the remainder of the venting apparatus. The tube has two opposite ends 18 and 20 which are open and inner and outer surfaces 22 and 24. The tube in one preferred embodiment comprises a SURGILAST® net which is a stretchable piece of fabric material having a significant amount of elasticity which allows the venting apparatus to be slid over the desired body part, i.e., a body part with a broken bone that must be kept immobile by means of a cast. This tube can preferably be adjusted in its diameter by twisting its end sections in opposite directions about its central axis.

The apparatus 10 further includes a plurality of elongate venting devices 26 which are also arranged in the form of an internal tube 27. The venting devices, which can each take a variety of forms as explained further hereinafter, are attached to the inner surface of the flexible tube 16 which can be a SURGILAST® tube. In other words, the tube 27 shown in FIG. 3 is located within the tube 16 in order to form the venting apparatus shown separately in FIG. 4. Each venting device 26 can, for example, be constructed in the manner shown in FIG. 5 and each venting device in this embodiment can extend from one open end of the tube 27 to the opposite open end in a spiral manner as illustrated in FIGS. 3 and 4. Each venting device 26 is arranged in a side edge to side edge manner relative to adjacent venting devices and they are connected to the exterior tube 16. Preferably the venting devices in this apparatus are not connected to one another so as to permit each venting device to move relative to adjacent venting devices when the tube 16 is twisted to adjust its diameter.

In a preferred embodiment of the venting apparatus 10, the internal diameter of the apparatus is sized so as to fit reasonably close to the exterior of the body part on which the venting apparatus is mounted. Because body parts differ in size, depending on such factors as the nature of the body part to be covered and the size of the person or animal requiring the cast, it is anticipated that the venting apparatus of the invention will be provided in at least several standard sizes. In this way, the doctor or veterinarian can use the venting apparatus 10 that is closest in size, i.e., internal diameter, to the width or diameter of the body part, normally selecting the venting apparatus which is slightly larger in its internal diameter than the body part. The apparatus can then be reduced in its diameter to fit the body part by twisting the tube 16.

Figure 2:
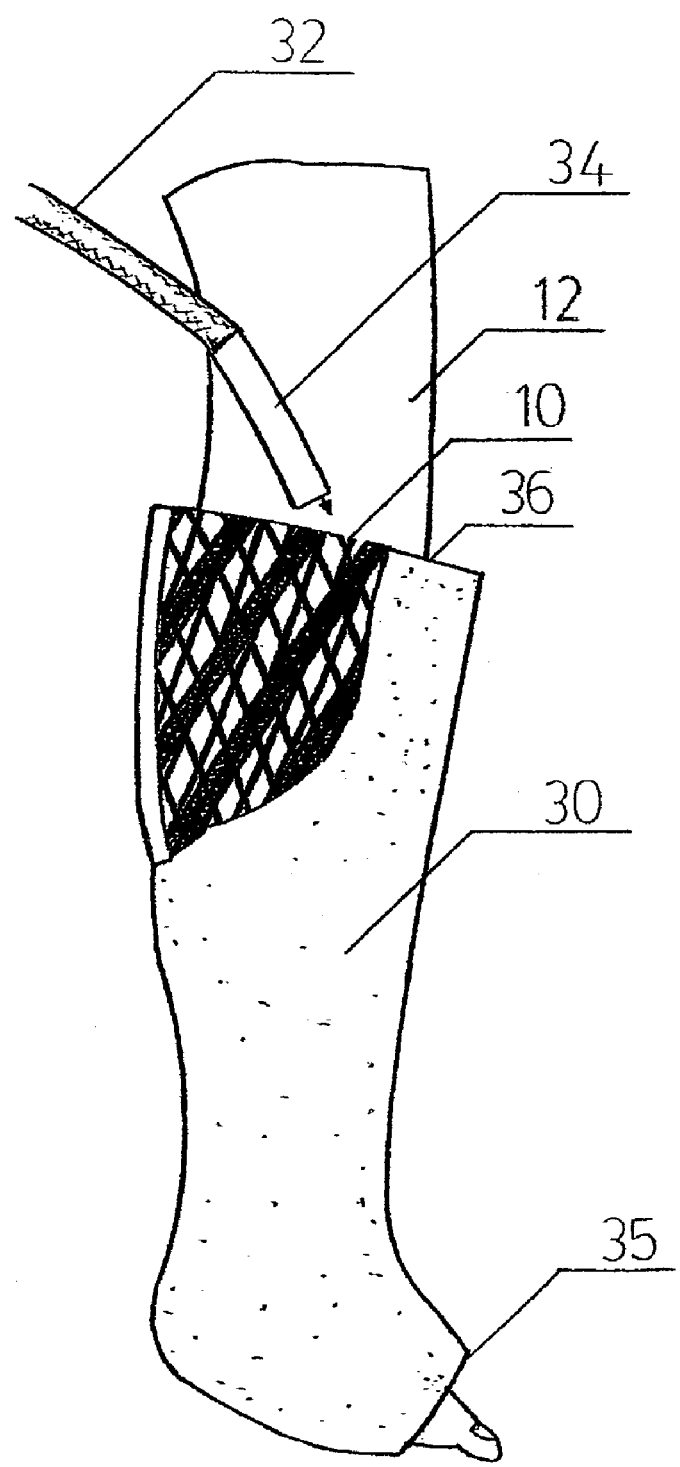
FIG. 2 is a schematic side elevation similar to FIG. 1 but showing a surgical cast formed on the venting device, a portion of the cast being broken away for sake of illustration.
Figure 6:
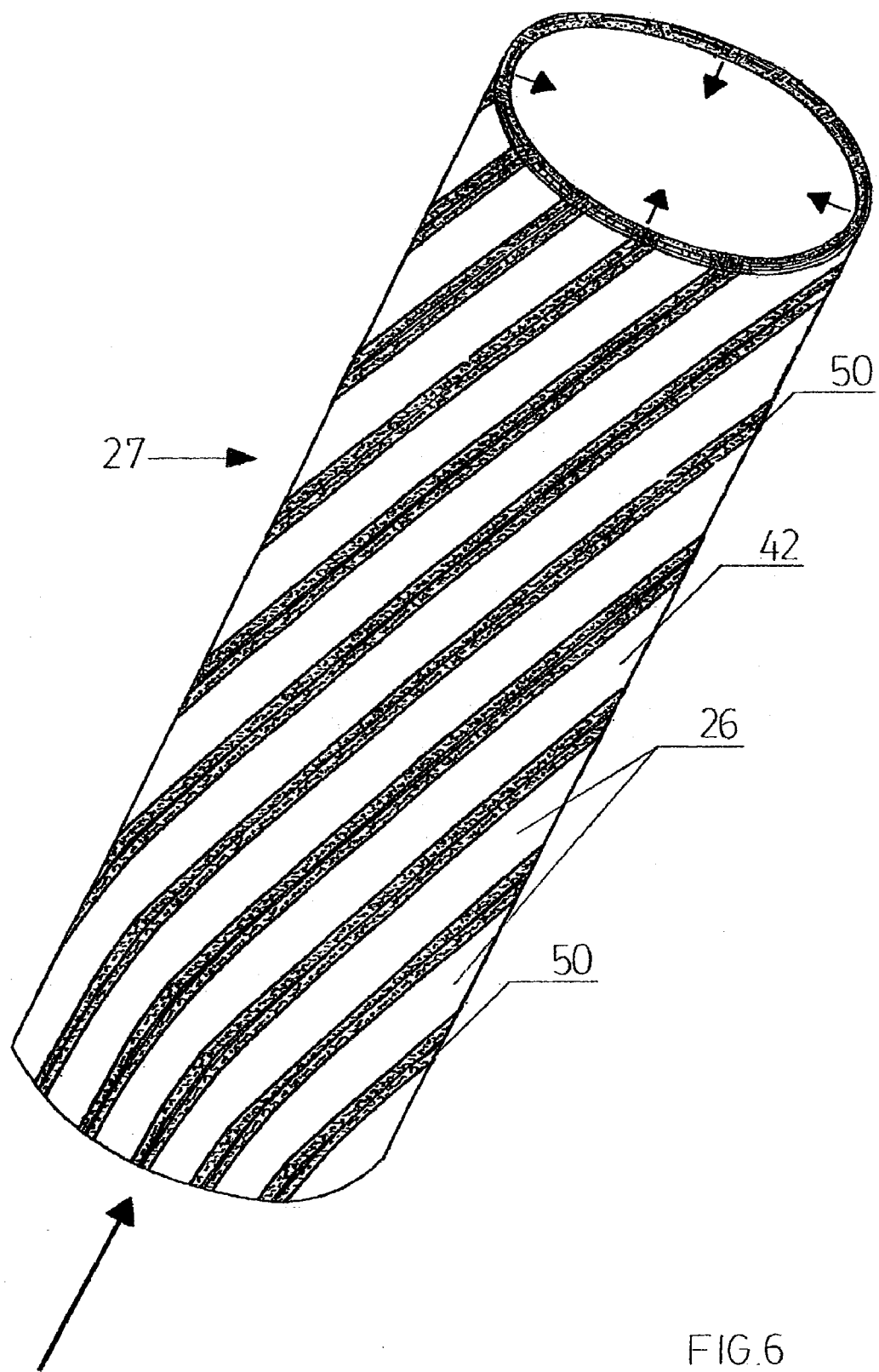
FIG. 6 is an isometric view of a plurality of venting devices arranged to form a tubular member with the outer, connecting net layer omitted for illustration purposes.

Turning to FIG. 2, this figure illustrates an actual rigid, surgical cast 30 that has been applied over the venting apparatus 10. The cast 30 itself can be of standard construction and can, for example, be made of plaster or resin. In a well-known manner, the rigid cast can be formed by wrapping a strip of impregnated cast forming fabric material around the venting apparatus in a layered fashion and then allowing the moistened cast forming material to harden or set. It will be appreciated that in the absence of the venting apparatus 10 of the invention, a known problem with a plaster or fiberglass cast is that the skin covered by the cast becomes irritated and itchy and this can cause great discomfort for the patient. This discomfort problem increases if the cast must be worn for a significant length of time and if the cast becomes wet and does not dry out properly. This discomfort can be lessened by supplying air under the cast and the use of the venting apparatus and venting devices of the invention can permit air circulation to the skin and removal of unwanted moisture under the cast. If desired, an air hose 32 such as that shown in FIG. 2 can be used to force or otherwise cause air under pressure to flow into one end of the venting apparatus 10. The hose 32 can be provided with a suitable nozzle 34 to help direct the pressurized air into the open ended passageways formed by the venting apparatus, as explained further hereinafter. This air circulation can be enhanced by leaving the rigid cast 30 open at both of its ends 35 and 36.

With particular reference to FIGS. 5, 6, 7 and 9 of the drawings, one preferred embodiment of the venting device 26 will now be described in detail. This particular venting device 26 which has a length and a width, includes two elongate strips 40 and 42 of flexible material. Preferably this material is also elastomeric. For purposes of the present description, the strip 40 will be described herein as the lower strip, being the strip closest to the skin surface when the venting device is used and the strip 42 will be described as the upper strip as it extends over the lower strip when the venting device is in use. At least the lower strip 40 is porous. As indicated in FIG. 5, the lower strip has numerous holes 44 distributed evenly along the length and width of the strip. It will be appreciated that these holes extend from the outer side of the strip to the inner side and they act to allow air to flow from the interior of the venting device to the adjacent skin of the patient. The strips 40 and 42 are spaced apart from each other and extend substantially parallel to each other, both lengthwise and widthwise. In one preferred embodiment of this venting device, the two strips are approximately $\frac{1}{8}^{th}$ of an inch apart. A preferred material for the lower strip 40 is ethyl vinyl acetate (EVA). If desired, the upper strip 42 can be made of the same material as the lower layer but it need not be porous and, in particular, the upper layer does not need to be formed with numerous holes 44 since the upper layer is covered with the rigid cast material during use of the venting device. Another porous elastomeric material that can be used for one or both of the strips 40, 42 is sold under the trademark NYPLEX®.

In addition, the venting device 26 includes flexible spacer members 46 arranged between the two strips 40, 42 and connecting these strips together. As illustrated in FIG. 5, there are two outer, elongate spacer members 46 that extend along the opposite, longitudinal edges of the strips 40 and 42 and a single, central spacer member 46. However, there can be several intermediate spacer members located between the outermost spacer members 46, if desired or if required. Generally speaking, the number of these elongate spacer members should be such as to prevent collapse of the air passageways 48 formed between the adjacent spacer members during use of the venting device. The spacer members 46, which can extend the entire length of the venting device 26, form the air passageways 48 so that air is normally free to pass along these passageways so as to permit air circulation substantially across the length and width of the venting device 26. It will be understood that at least one end and preferably both ends of these air passageways are left open so as to promote the circulation of air. It will be understood that the preferred spacer members 46 are solid members as this helps prevent collapse of the air passageways 48 when the venting device is put into use and a cast is applied, but it is also possible for the members 46 to be hollow tubes of either square or cylindrical cross-section. The solid members may also be less expensive to use than tubular members. The spacer members can also be perforated (not shown) or imperforate.

A further significant component of the venting device 26 is a porous fabric layer 50 that extends in a longitudinal direction along an outer side of the lower strip 40 opposite the spacer members 46 and covers the outer side of this strip. This fabric layer is attached to the strip 40 and can, for example, be bonded by a suitable adhesive to the strip 40 in a manner which allows moisture and/or air to pass through the adhesive layer. In one preferred embodiment, the fabric layer 50 is moisture-absorbent and made of cotton. Preferably this layer at least partially covers opposite side edges of the venting device 26 that extend between the outer sides of the elongate strips 40, 42. In the embodiment of FIG. 5, the fabric layer covers completely these opposite side edges by side edge sections 54. The layer 50 can serve a couple of major functions when used on the present venting device. Firstly, if the layer is made of moisture-absorbent or hydrophilic material, the layer can absorb any moisture build-up on the user's skin as a result of sweating or otherwise. Secondly, it can increase the comfort level of the venting device during its use under the cast as the layer 50 can be made soft and compatible with the skin of most users. However, the layer 50 can also be made of hydrophobic fabric materials or a combination of hydrophilic and hydrophobic materials, the selection depending on the characteristics and advantages desired. For example, it may be desirable to use a hydrophobic material if the cast and venting device are likely to get wet while being worn. The cast may need to get wet for instance if the patient requires hydrotherapy.

Because the spacer members 46 are covered by the two layers 40 and 42, it is possible to construct these members from a variety of flexible materials, including flexible plastics. In one preferred embodiment, these spacer members are also made of ethyl vinyl acetate (EVA) so that they will bend and stretch in the same manner as the lower and upper strips 40, 42 made of the same material. A variety of "EVA" type products are currently available and can be used in the venting device of the invention. These include VOLARA® 4E™ ALIPLAST™ (both of 23 durometer), P-CELL™ (20 durometer for diabetics), and MICROCELL® PUFF™ (25 durometer). Another suitable, flexible material for this purpose is PORON®, a Medical 4708 urethane polymer.

Figure 7:
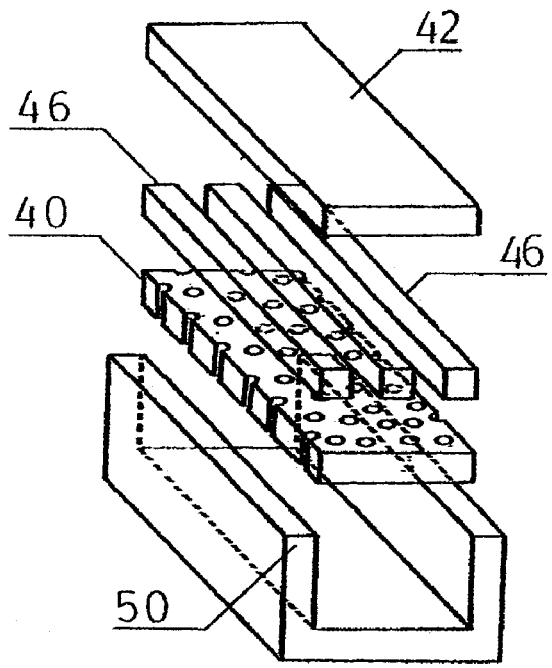
FIG. 7 is an isometric detail view showing the individual components of a first form of venting device shown separated from one another for sake of illustration.
Figure 8:
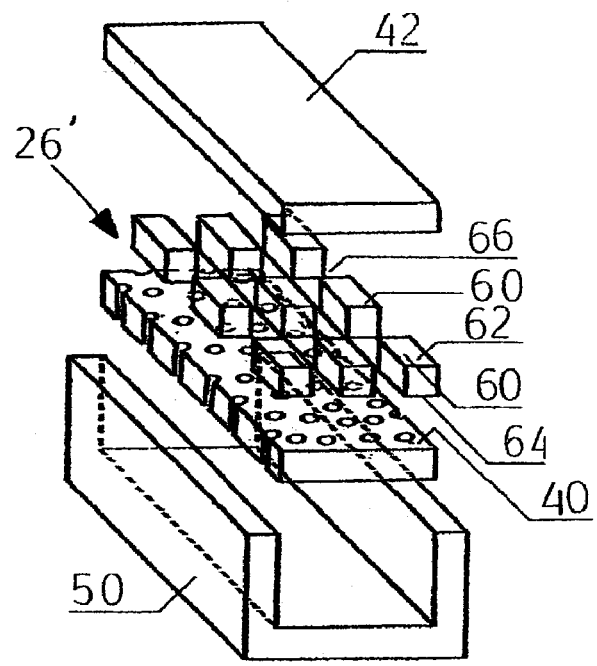
FIG. 8 is an isometric detail view similar to FIG. 7 but illustrating an alternative form of venting device.

In the embodiment illustrated in FIGS. 5 and 7, the spacer members 46 are solid and elongate members and the air passageways 48 formed between them extend longitudinally so that air is free to pass along the length of the strips 40, 42 from at least one end of these strips. However, a different form of spacer members is illustrated in FIGS. 8 and 11a-11b. In this venting device indicated generally by 26', the lower and upper strips 40, 42 are constructed in the same manner as the embodiment of FIG. 7. However, in this embodiment, the spacer members indicated by 60 comply a plurality of relatively small blocks (preferably solid) arranged in a plurality of parallel longitudinal rows. The illustrated preferred blocks 60 are formed with flat sides, including substantially flat top sides 62 and bottom sides 64. It will be understood that because the top and bottom sides are substantially flat, this makes it easier to bond these blocks to the adjacent lower and upper strips by means of a suitable adhesive. One advantage of using the small blocks 60 rather than the elongate spacer members 46 is that the air gaps 66 formed between adjacent blocks in each row permit air circulation in the widthwise direction. Also, the use of the blocks 60 can enhance the ability of the elongate venting device to bend along its central, longitudinal axis, particularly if the venting device is being bent in two directions in order to form a spiral.

Also, shown in FIGS. 11a and 11b is the use of a porous fabric layer 50 that extends only part way up the side edges of the venting device. In particular, the fabric layer has only short, upstanding edge strips 68 and 70 which extend the entire length of the venting device 26'. These edge strips cover the longitudinal side edges of the porous layer 40. Again the layer 50 can be hydrophobic or hydrophilic and it may comprise more than one layer as explained below.

Figure 24:
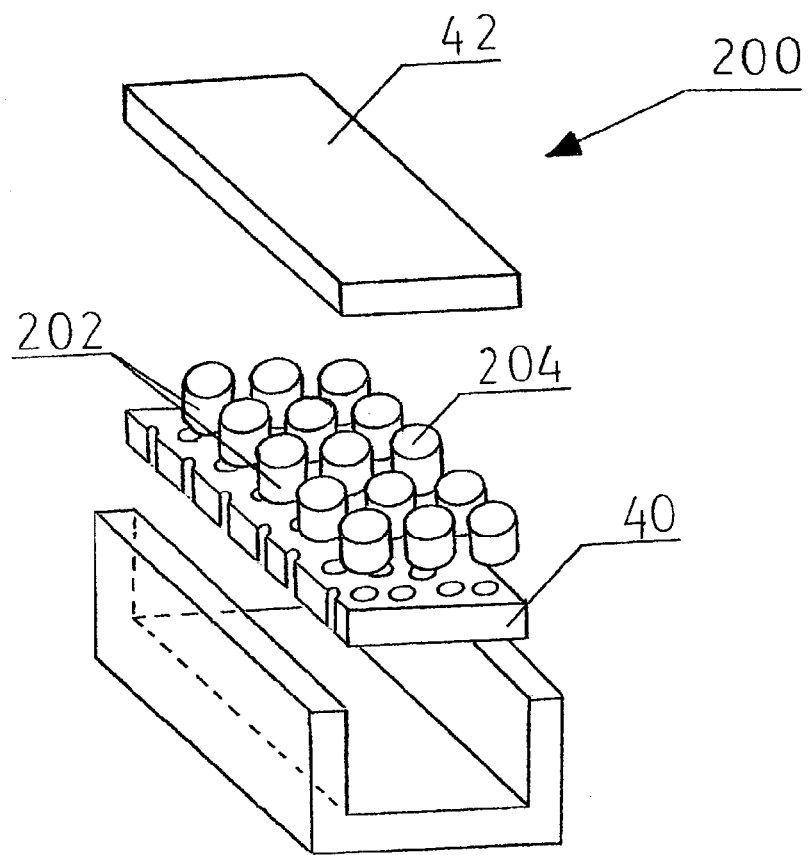
FIG. 24 is another isometric detail view showing a variation of the venting device of FIGS. 11a and 11b.

A variation of the venting device of FIGS. 11a and 11b is shown in FIG. 24. This venting device 200 is the same as the venting device 26' except for the shape of the small spacer members 202 which are cylindrical. The members 202 have flat, circular ends 204 which are bonded to the two layers 40 and 42.

Figure 14:
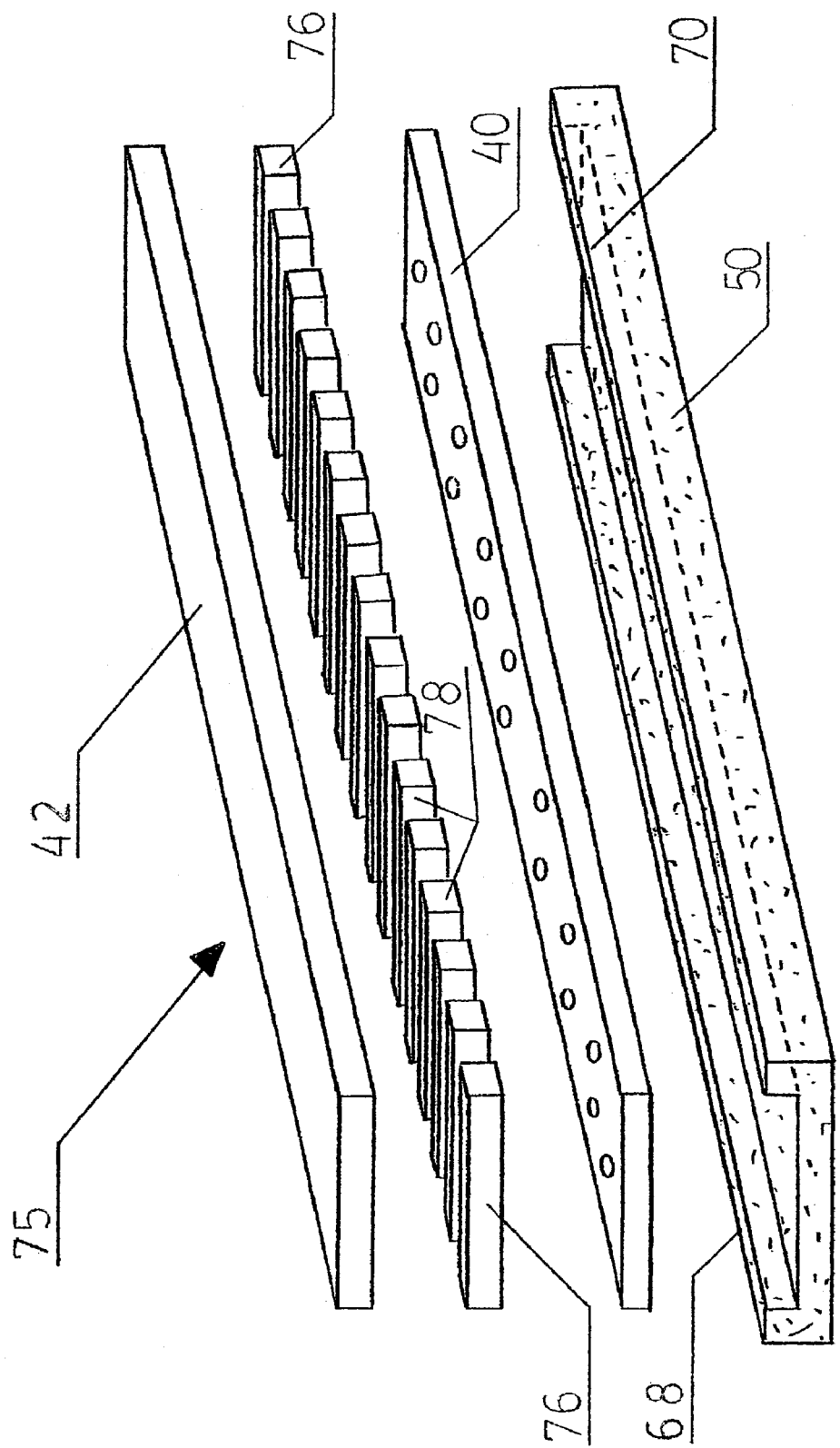
FIG. 14 is an isometric view illustrating another form of venting device with the components separated from one another for illustration purposes.

Another form of venting device constructed in accordance with the invention is illustrated in FIG. 14. This embodiment indicated generally by reference 75 is similar to the venting device 26 in its construction except for the arrangement of the spacer members. The venting device 75 includes an elongate upper strip 42 and an elongate lower strip 40 which is porous. These two strips are spaced apart by and connected by a plurality of elongate spacer members 76. These spacer members extend transversely of the elongate strips 40, 42 and they can extend the entire width of these strips as shown in FIG. 14. As before, the spacer members are elongate blocks that are flexible so that they can bend as required. These spacer members are preferably solid blocks and can be either imperforate or perforated with numerous small holes (not shown). Air passageways 78 are formed between these spacer members and these also extend transversely relative to the elongate strips 40, 42. By means of these passageways, air is free to pass across the width of the elongate strips from side edges of the venting device 75. The venting device 75 also has the porous fabric layer 50 that can be hydrophilic and made of cotton or hydrophobic. As shown, this layer extends in a longitudinal direction along the outer side of the lower strip 40, that is the side opposite the spacer members 76. Again, the fabric strip 50 is attached to the strip 40, for example by means of a suitable adhesive or by stitching (not shown). The illustrated fabric layer 50 in FIG. 14 also has side edge strips 68 and 70 which have a height corresponding to the thickness of the lower strip 40.

Figure 12:
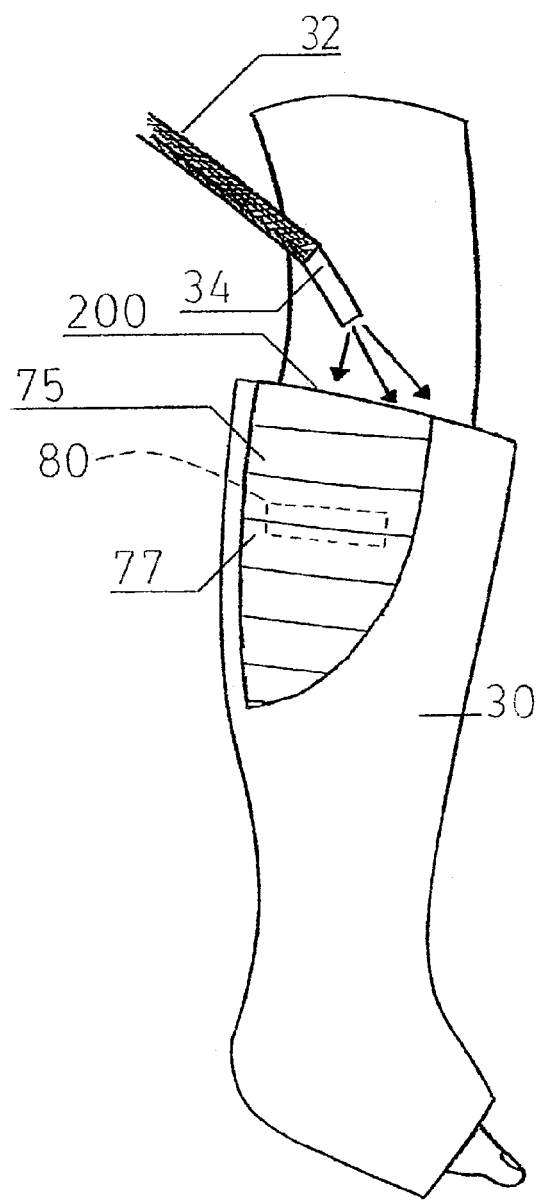
FIG. 12 is a schematic side elevation showing the use of one form of venting device applied to a person's leg and foot with a surgical cast applied over the venting device and partially broken away for illustration purposes.
Figure 13:
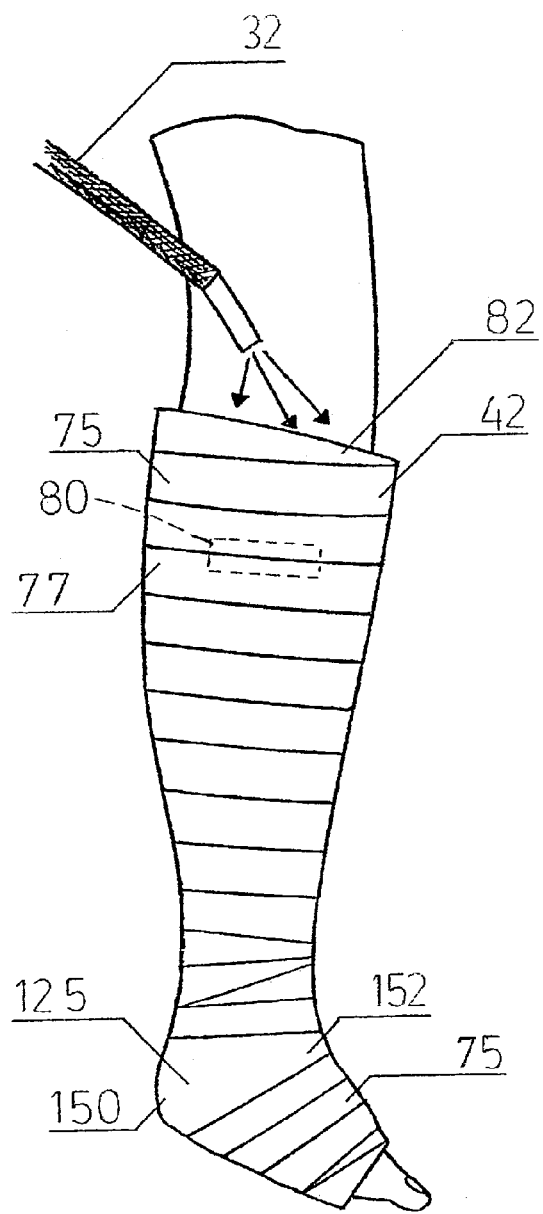
FIG. 13 is a schematic side elevation similar to FIG. 12 but without the surgical cast applied over the venting apparatus which, in this case, comprises several venting devices connected to one another.

The venting device 75 is particularly useful when used under a cast 30 in the manner illustrated in FIGS. 12 and 13. In particular, the venting device 75 can be used without an attached tube 16 so that the upper layer 42 of the device is directly under and supports the cast material. As shown, the elongate venting device can be wrapped around a body part, such as a leg, in a spiral fashion until a required area of the body part is covered. Each coil or wrap 77 of the venting device has its side edges placed immediately adjacent to the side edges of the adjacent coils in order to form a continuous, uninterrupted surface over which the flowable cast material can be applied to form the cast. As explained further hereinafter, these coils can be held in place relative to one another by suitable fastening devices that extend along the edges of the adjoining coils in order that the coils will remain in place until the cast material has been applied and has hardened. Because the spacer members 76 extend transversely, air can flow between the adjacent coils from one open end 200 of the wrapped venting device to the opposite open end. In other words, a sufficient number of the passageways 78 in each coil will be aligned with the adjacent passageways of the adjacent coil to permit air to circulate sufficiently through the venting device from one end of the cast to the opposite end. Again, this air circulation can be increased or enhanced by the use of an air hose 32 as shown attached to a suitable nozzle 34.

One form of attachment of the adjacent coils comprises well-known surgical tape, a strip of which is indicated in dash lines at 80 in FIGS. 12 and 13. Although this tape is shown extending in the lengthwise direction of the joint between two coils, it is also possible to apply the surgical tape transversely of the coils. The tape is attached to the upper strips 42 or, if no upper strips 42 are used (see below) the tape can be attached to the spacer members 46 or 60. Also illustrated in FIGS. 12 and 13 is the fact that each end of the venting device 75 can be tapered as at the upper end 82. This can be accomplished by the medical person, who is applying the venting device, by simply cutting the soft materials of the venting device 75 so as to form the tapered end. In this way, the end of the wrapped venting device can extend in a plane that is substantially perpendicular to the center axis of the limb. This may be preferred if the medical practitioner wants the end of the cast to extend in a plane that is perpendicular to the central axis of the limb.

Figure 10:
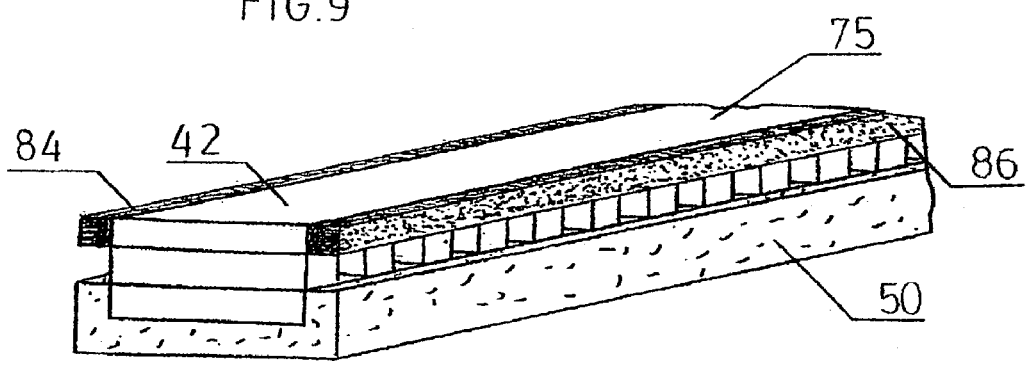
FIG. 10 is an isometric view of another form of venting device provided with hook and loop type fastener strips along its upper longitudinal edges.

Another way of attaching adjacent coils of the venting device 75 is illustrated in FIG. 10. In this version, multiple hook and loop type fasteners, commonly sold under the trademark VELCRO®, are attached to opposite side edges of the upper strip 42. These elongate fastener strips are indicated at 84 and 86 and it will be understood that they can extend the entire length of the venting device 75 or each fastener strip can be broken into shorter sections with gaps between the ends of the sections. The gaps should not be so large as to not allow adjacent coils to be firmly connected to one another in a manner that avoids gaps between the adjacent coils. Preferably, the height of the fastener strips 84, 86 as measured in the plane of the outer surface of the strip 42 should not be so great as to prevent adjacent edge sections of the fabric layer 50 from resting against one another. In other words, the fastener strips should be constructed and arranged so as to allow the fabric layers 50 of adjacent coils to form a continuous inner surface when the fastening devices are connected together. Of course, when the hook and loop type fastener strips are used, the fastener strip along one side of the venting device comprises multiple hooks while the opposite fastening strips comprises multiple loops since the hooks are constructed to engage with and connect firmly to the loop strip in a well known manner.

Another way in which the adjacent loops of the venting device can be connected together is by means of a zipper fastener, such as the zipper fastener 90 illustrated in FIG. 19. The use of this type of fastener will be described later in connection with another embodiment of this invention.

With particular reference to the venting device 26 shown in FIG. 5, in this device the side edge sections 54 are shown as extending perpendicular to the lower strip 40. It is also possible for the side edge sections to extend at an acute angle, say in the order of 60 degrees, to the lower strip 40. In order to make the venting device with these angled sides, the side edges of the layers 40 and 42 can also be angled in a similar manner as can the sides of the spacer members, particularly the spacer members extending along the longitudinal edges of layers 40 and 42. An advantage of arranging the sides of the venting device at an acute angle to the bottom surface is that the angled sides will help to hold the coils of the wrapped venting device in place since a side edge section 54 of one loop or coil will overlap to some extent the adjacent side edge section of the next loop or coil.

Another embodiment of a venting device constructed in accordance with this invention is illustrated in FIGS. 15 and 16. This venting device indicated generally at 92 is similar to the venting device 75 except for the differences noted hereinafter. Thus, the venting device 92 includes a lower elongate strip 40 made of porous, flexible material and having an inner side 94 and an outer side 96. This strip also has opposite side edges 97 and 98 extending between opposite ends of the strip. There are also spacer members 78 which are connected to the inner side of the strip 40 and which extend transversely of the strip and have a length substantially equal to the width of the strip 40. Mounted on these spacer members are a series of substantially flat, flexible outer members 100 which are arranged in a row from one end of the strip 40 to the opposite end thereof. The preferred illustrated outer members are flat sided and rectangular or square as seen from above. In particular, they have a normally planar inner side 102 and a normally planar outer side 104 and they also have opposite side edges 105 and 106, the height of which can be approximately the same as the height or thickness of the strip 40 as shown. In one preferred embodiment, the thickness of the strip 40 is about 2 mm. The inner sides 102 of the outer members 100 are spaced a substantially uniform distance from the inner side 94 of the strip 40. As can be seen clearly from FIG. 16, the opposite side edges 97, 98 of the strip 40 and the opposite side edges 105, 106 of the outer members are substantially aligned with one another in a transverse direction which is perpendicular to the inner side of the strip 40. Again, the spacer members 78 form elongate air passageways 108 that extend across the width of the venting device, these passageways permitting air to normally pass therethrough so that air circulation is permitted over the length and width of the venting device.

As in the previous embodiments, there is also a porous fabric layer 50 extending in a longitudinal direction of the venting device and extending along and covering the outer side of the elongate strip 40. Again, this fabric layer 50 is attached to the elongate strip and this can be done by means of adhesive bonding or by stitching (not shown). The illustrated fabric layer 50 shown in FIGS. 15 and 16 also covers the side edges 97 and 98 of the layer 40. The fabric layer can be cotton assuming a hydrophilic material is desired.

As shown in FIG. 16, the outer members 100 can be sized and arranged so as to form uniform air gaps 110 between adjacent members or blocks. However, these gaps are not essential for this version of the venting device and, in fact, the adjacent surfaces 112 of adjacent members 100 can be immediately adjacent to or in contact with each other when the venting device 92 is at rest and has not been bent or twisted. One advantage of the venting device 92 is that this venting device is easily able to bend and adapt to the curvature of a body part such as an arm or a leg because there is no continuous upper strip 42. In other words, the only components of this embodiment that must bend substantially in order to conform to the body part or limb is the flexible layer 40 and the fabric layer 50 of cotton or other materials. As this venting device 92 is bent around the limb, the outer members 100 will simply separate from one another in the longitudinal direction of the device or will become further apart. In other words, the width of the air passageways 108 will increase in size. Because the members 100 are able to separate from each other as the venting device is bent, the members 100 can be made of a less flexible material or a material which is not elastomeric, if desired.

It is also possible to provide a venting device like that shown in either FIG. 11*b* or FIGS. 15 and 16 but without the upper strip 42 or the outer members 100. With a venting device of this type the cast material is wrapped directly over the spacing members, i.e., members 60, 76, and then allowed to set. In this case, the spacing members must be sufficiently high and rigid to maintain the air passageways between them after the cast material is wrapped. It is also possible to construct a venting device of the invention without the upper strip 42 or outer members 100 using the three dimensional textile fabric taught and illustrated in U.S. Pat. No. 5,882, 322 issued Mar. 16, 1999, the specification and drawings of which are incorporated, herein by reference. This textile fabric has a base plane formed by the fabric and a multiplicity of projections made of the same textile fabric that are resilient and rise above the base plane. This three dimensional fabric can, for example be substituted in place of the lower strip 40 and the spacer members 46 in the venting device of FIGS. 5 and 7 or in place of the lower strip 50 and blocks 60 in the device of FIG. 8. When using this three dimensional textile fabric, the cast maker must wrap the settable cast material carefully so that the wrapped cast material stays on top of the projections and does not unduly enter the space between the projections or rest against the fabric comprising the base plane. If this three dimensional textile fabric is used, the textile material is preferably perforated with numerous small holes over its entire area.

Figure 17:
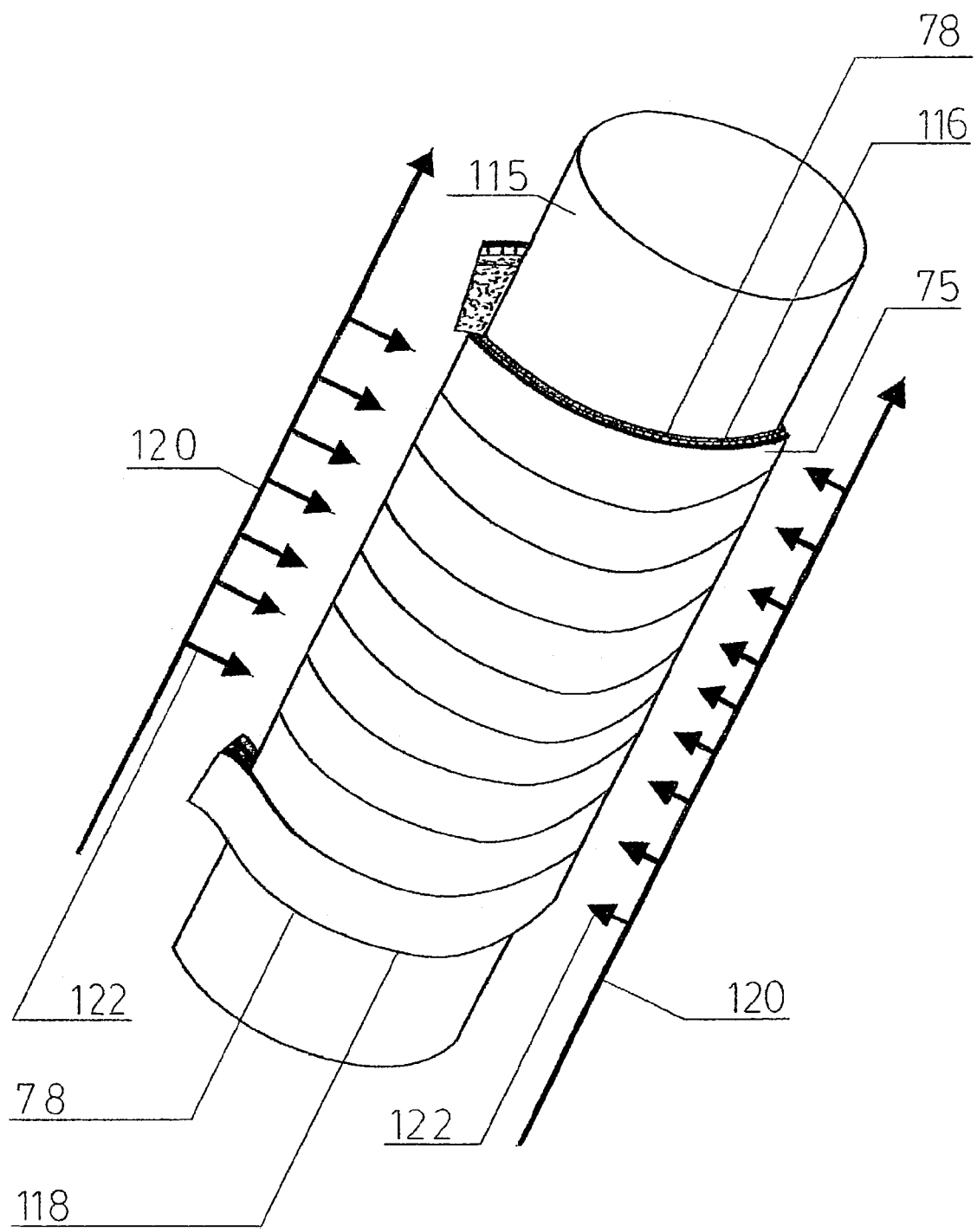
FIG. 17 is a schematic side view illustrating how the venting device of FIG. 14 can be applied to a person's limb in a spiral manner and illustrating the air circulation in the venting device.

FIG. 17 illustrates schematically how the air circulates through a spirally wrapped venting device 75 that has been applied to an elongate limb having a generally cylindrical exterior, this limb being indicated schematically at 115. The venting device 75, as already described, can be constructed with transversely extending air passageways and thus there are open air passageways 78 at both the upper end 116 of the wrapped venting device and at the bottom end 118. A number of the passageways 78 are open to similar passageways 78 in the adjacent coil or coils and this permits an air stream indicated by the long arrows 120 to pass from one end of the coiled venting device to the other end. Although the illustrated arrows 120 show this air flow as passing from the end 118 to the end 116, the air flow could of course be in the opposite direction or could in some cases be in both directions. The shorter arrows 122 that extend from the arrows 120 illustrate schematically how the air flow turns 90 degrees in the passageways 78 to pass through the lower strip 40 and the porous fabric layer 50 to the skin of the limb or body part. Thus, this type of venting device can provide good air circulation to most regions of the skin below the cast when it is used.

FIG. 18 illustrates a modified form of surgical cast venting device constructed in accordance with the invention. This venting device indicated generally at 125 is similar in its construction to the above-described venting device 75, except for the differences noted hereinafter. The venting device 125 can be employed where there is a significant bend or curve in the body part to be enclosed in the cast or orthopedic device. With reference to FIG. 13, a venting device similar to the device 125 can be employed, for example, in the region of the heel of a patient where the cast 30 is to extend over the heel. It could also be used at an elbow if the arm is bent. In particular, the coiled venting device 75 can be connected at its bottom end to the venting device 125 by means of surgical tape in order to prevent any gaps between the ends of the two venting devices. If desired, and as an extra precaution, a layer of cotton or other suitable fabric can be wrapped around the limb where the two venting devices will be joined prior to application of the two venting devices. This extra layer of cotton or fabric can be held in place by means of a small amount of surgical tape or by stitching.

Turning now to the construction of the venting device 125, this device, which has a length and a variable width, includes an elongate, first layer 126 of porous, flexible, elastomeric material, this layer corresponding to the lower strip 40 of the above described embodiments. The venting device also has an elongate, second layer 128 of flexible, elastomeric material extending over and substantially covering the first layer 126. This second layer is spaced a substantially uniform distance from a top side 130 of the first layer. The second layer has a wide, central longitudinal section 132 and two relatively narrow end sections 134 and 136 extending from opposite ends of the central longitudinal section 132. It will be understood that the first layer 130 is similar in its shape, length and width as the illustrated second layer 128. Thus, the first layer 130 also has a wide, central longitudinal section with curved side edges and two relatively narrow end sections extending from opposite ends of its central longitudinal section. Small portions of the central longitudinal section 138 of the first layer can be seen in FIG. 18.

Spacer members 140 are arranged between and connect the first and second layers 126, 128. These spacer members can extend transversely of the venting device 125 and they can vary in length, being longer in the central section of the venting device. As before, the spacer members 140 form air passageways 142 between the adjacent spacer members so that air can normally pass along these passageways so as to allow air circulation over the length and width of this venting device. The venting device 125 is also provided with a moisture-absorbing, porous fabric layer indicated by reference 144 in this embodiment or, in the alternative, the layer 144 can be a hydrophobic fabric. This fabric layer extends in a longitudinal direction along and covers a bottom side of the first layer 126. The fabric layer 144 is attached to the first layer, preferably by an adhesive bond, and it also can be provided with upwardly projecting edge sections 146 and 148 which cover the longitudinal edges of the first layer 126. The dotted lines in FIG. 18 indicate that the two end sections 134, 136 can vary in length and can be much longer than the short end sections illustrated in solid lines in FIG. 18. It will be appreciated that with this venting device 125, the wider central section of the venting device is placed over the outside of the curve or bend in the body part. In the case of a heel to be covered, the wider central section is placed at the location 150 in order to accommodate this bend. The narrower end sections 134, 136 are then used to cover the inside of the bend at 152. The overall length of the venting device 125 can, of course, be adjusted by trimming the length of the two end sections 134, 136 so that the venting device will fit the bend in the body part. Again, it is possible to trim the ends of end sections 134, 136 so that they are appropriately tapered and form an end circle that extends perpendicular to the central axis of the straight portion of the limb. In this way, the opposite ends of the wrapped venting device 125 can be matched up with the adjacent ends of coiled venting devices 75. Incidentally, the complete venting apparatus shown in FIG. 13 can comprise a first coiled venting device 75 covering the bottom portion of the leg, a venting device 125 used in the heel region and a second, shorter coiled venting device 75 used to cover the central region of the foot. As indicated, all three of these venting devices can be connected to each other on the outside thereof by surgical tape or, if desired, by VELCRO® strips (as described above).

An alternate way of accommodating a bend in the body part, such as heel, is to mold a special venting device so that it will fit snugly and exactly around this bent portion of a particular patient. In order to make a venting device of this type, the supplier of the venting device would create a mold of the bent section of the body part about which the cast is to extend, a layer of EVA material or other suitable, flexible material is then applied to this mold in a flowable form and so as extend around the portion of the mold representing the bend in the body part. This layer of EVA is then allowed to harden and because it is flexible, it can then be readily removed from the mold and then the remainder of the venting device can be constructed in the manner of the venting devices already described, for example, in the manner of the venting device 125. This customized venting device can then be readily applied in a snug fitting manner to the bent portion of the body part prior to application of the cast material.

Another possible way of accommodating significant bends in the body part to be covered is by the use of first and second layers 126, 128 in the venting device made of a material which is quite stretchable or elastomeric. One such material that is currently available is sold under the trademark NYPLEX®. By using material of this type, the venting device will readily bend to accommodate either the inside corner or the outside corner of a substantial bend in the body part.

Figure 20:
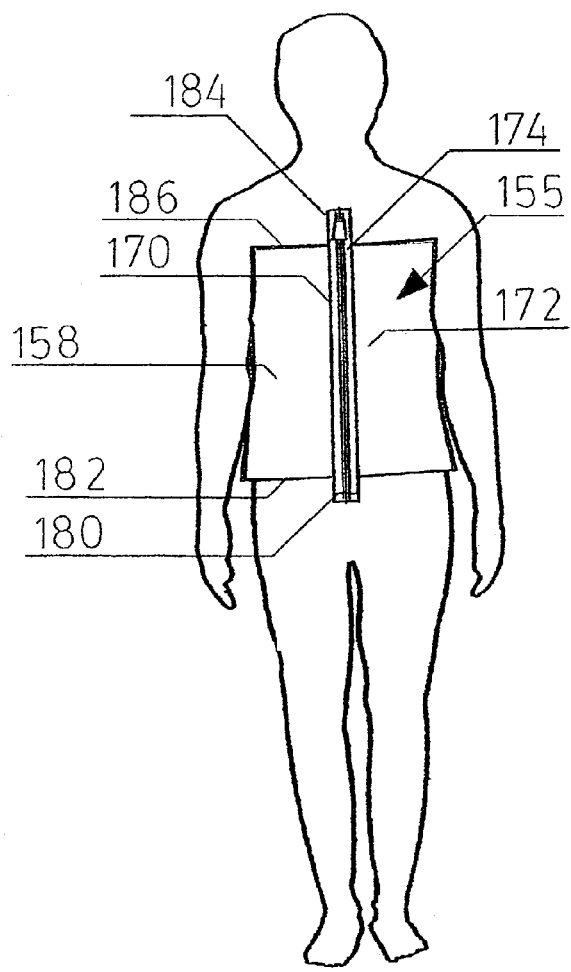
FIG. 20 is a front view of another venting device adapted to cover a person's torso.
Figure 21:
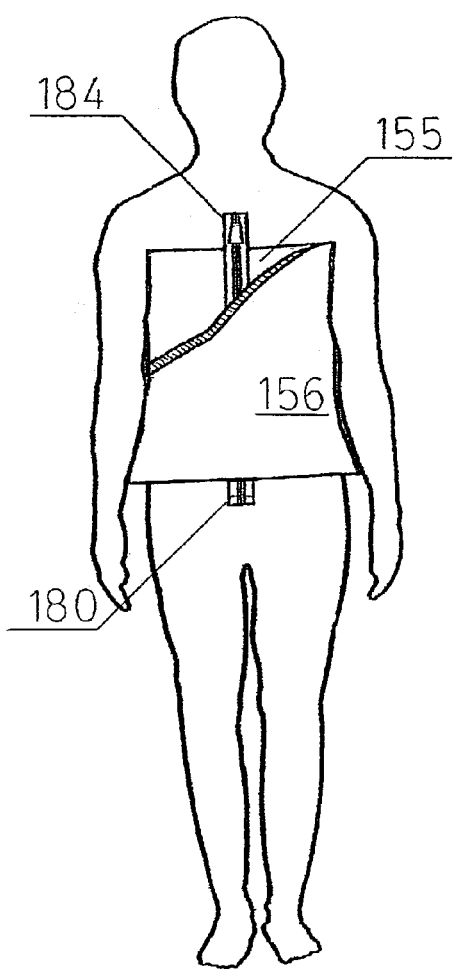
FIG. 21 is a front view similar to FIG. 20 but showing a rigid body cast applied over the venting device.

FIGS. 20 and 21 illustrate how another embodiment of venting device can be constructed and used under a cast. This venting device indicated generally at 155 can be used, for example, under a body or torso cast 156. This body cast is illustrated in FIG. 21 and a portion of the cast has been broken away for sake of illustration in this figure. This venting device 155 differs from the above described venting devices which employ relatively narrow strips of material 40, 42 in that it is made of relatively wide, inner and outer layers of flexible material, including an outer layer 158. End sections only of these two layers are illustrated in FIG. 19. It will be understood that these two layers which are of similar size, are made sufficiently large in their length and width to permit them to be wrapped around the body part such as the torso and to permit the opposite ends of the venting device to be connected together by a suitable fastening mechanism or fastening device. Edge sections of the inner layer 160 can be seen in FIG. 19. The two layers extend substantially parallel to each other and the material of at least the inner layer 160 is porous and preferably covered with numerous holes that extend completely through this material (as in the previous embodiments). Flexible solid spacer members 162 are arranged between and connect the two layers and these members form air passageways 164 between adjacent spacer members 162 so that air is normally free to pass along these passageways from one or more open edges of the venting device 155. Again, a porous hydrophilic or hydrophobic fabric layer 166 extends over and covers an outer side of the inner layer 160 and this fabric layer is attached to the inner layer. Again, preferably the fabric layer 166 is formed with upstanding edge strips 168 that cover the adjacent edges of the inner layer 160 and that can also cover adjacent spacer members, if desired. In some embodiments, not including the illustrated embodiment employing a zipper, the edge sections 168 of the fabric layer can extend up to the top edge of the outer layer 158. For example, the edge sections 168 can extend up to the top of the outer layer if the adjacent edges of the wrapped venting device are joined by a strip or strips of surgical tape prior to application of the cast material.

In one preferred embodiment of the venting device 155, opposite side edges 170 and 172 of the outer layer 158 can be connected together by means of a zipper fastener indicated generally at 174. The zipper fastener 174 includes elongate fastener devices 175 and 176 that extend along and are secured to the opposite side edges of the outer layer. In the zipper version, these fastening devices 175, 176 are the two opposing sections of the zipper which itself can be of standard construction. Thus, with the use of this zipper fastener, the opposite side edges of the outer layer 158 can be connected to each other or possibly to side edges of another similar venting device (if more than one such device is required to wrap the desired area), after the venting device or venting devices have been wrapped around the body part which may, for example, be the torso as shown. Of course, instead of a zipper fastener, the elongate VELCRO® type fastening devices using multiple hooks and loops on the opposing fastener strips can be used. The use of such multiple hook and loop type fasteners has already been described above in conjunction with the venting device of FIG. 10.

If a zipper type fastener is to be used, the ends of the zipper should extend beyond the side edges of the venting device 155 as illustrated in FIGS. 20 and 21. In other words, a short bottom section 180 of the zipper extends below the side edges or bottom edge 182 of the venting device, while a short upper section 184 of the zipper extends above the side edge or upper edge 186 of the venting device. The reason for this arrangement is to avoid having these end sections of the zipper below the cast 156 after the cast has been applied. This will avoid discomfort that could be caused by pressure on these end sections if they were under the cast.

With respect to the venting device of FIGS. 19 and 20, a preferred method of attachment of the zipper fastener to the edges of the upper layer is by means of stitching using a suitably strong thread. It is also possible to connect the zipper fastener by means of a suitable adhesive.

Figure 22:
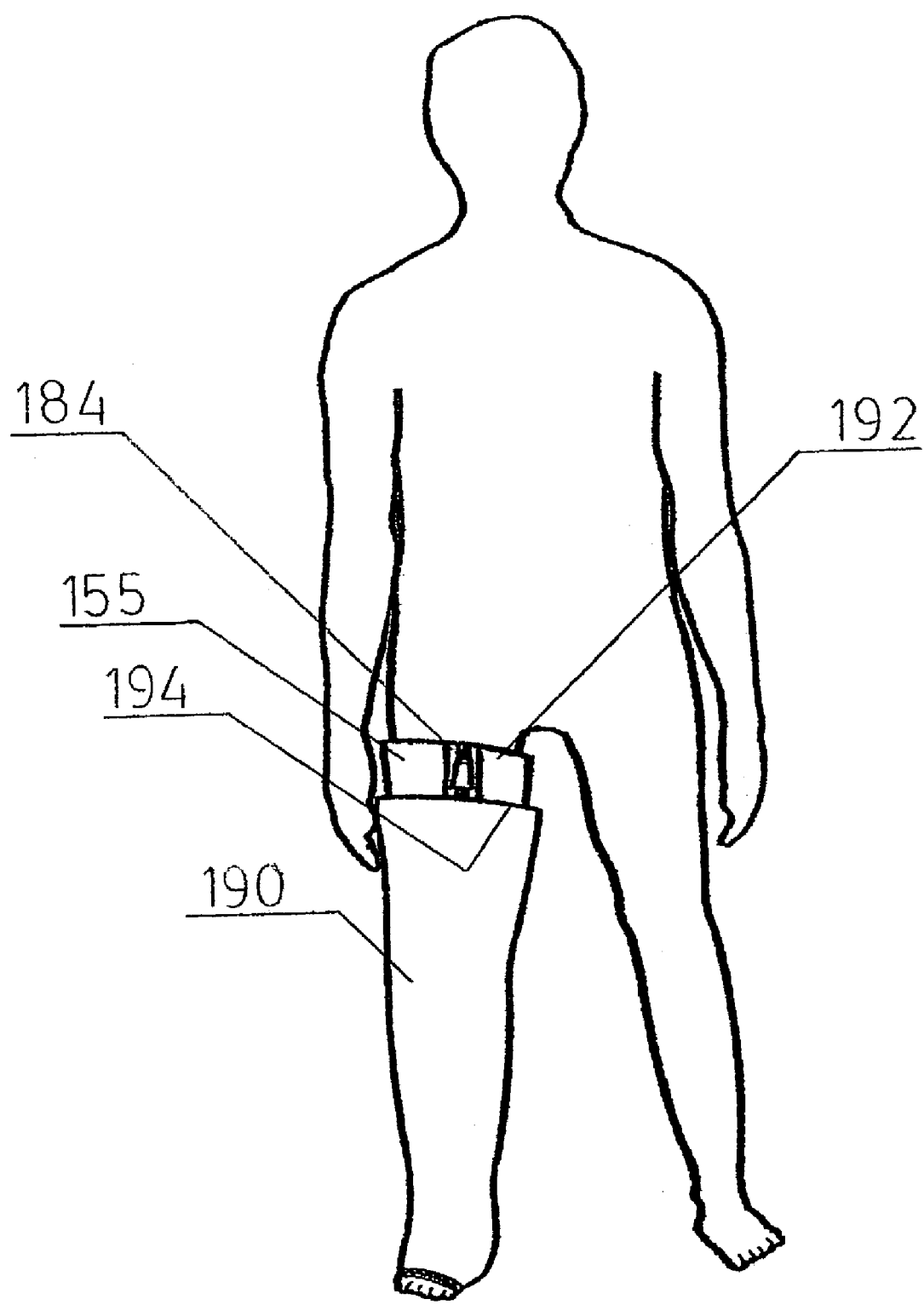
FIG. 22 is a front view showing a venting device similar to that of FIG. 20 but sized to fit and applied around a person's leg and foot.

FIG. 22 illustrates another possible application of a venting device 155. In this case, the venting device has been wrapped around the leg of a person and extends around the heel and a portion of the foot as well. The venting device is covered by a leg cast 190. In the illustrated arrangement, not only an upper portion 184 of the zipper fastener extends above the top of the cast but also an upper end section 192 of the venting device 155. In some cases, it may be desirable for the venting device to extend above or out from the end of the cast as this arrangement may be more comfortable for the person to move with the cast. Of course, it is also possible for only the upper end section of the zipper to extend above the top edge 194 of the cast and for the layers of the venting device to end at the adjacent edge of the cast. It will be appreciated that various body parts of either humans or animals can be covered using the venting devices and venting apparatus of the present invention.

When a zipper fastener is used, it is important that the fastener be mounted on the edges of the outer layer so that when the fastener is closed or secured, no gap is left between the adjacent edges of the venting device 155. For this reason, the zipper sections 175, 176 are preferably located directly above the cotton edge sections 168 and they project from the outer layer a distance similar to the thickness of the cotton edge strips. Because the cotton edge strips do not extend beyond the top of the spacer members, there is a gap above these edge sections 168 to accommodate the thickness of the zipper sections. In this way, no discomfort to the wearer is caused at the location of the zipper when the rigid cast has been arranged on the venting device.

Also, in the venting device 155, it will be appreciated that the spacer members 162 can be in the form of small, spaced apart blocks of generally rectangular shape with flat sides (as used in the venting device of FIG. 11a, for example). In this way the air can circulate readily across both the length and width of the venting device 155. Alternatively, it is also possible for the spacer members to be elongate members that extend the entire length of the venting device 155, for example, from its top edge to its bottom edge as shown in FIG. 20.

Figure 23:
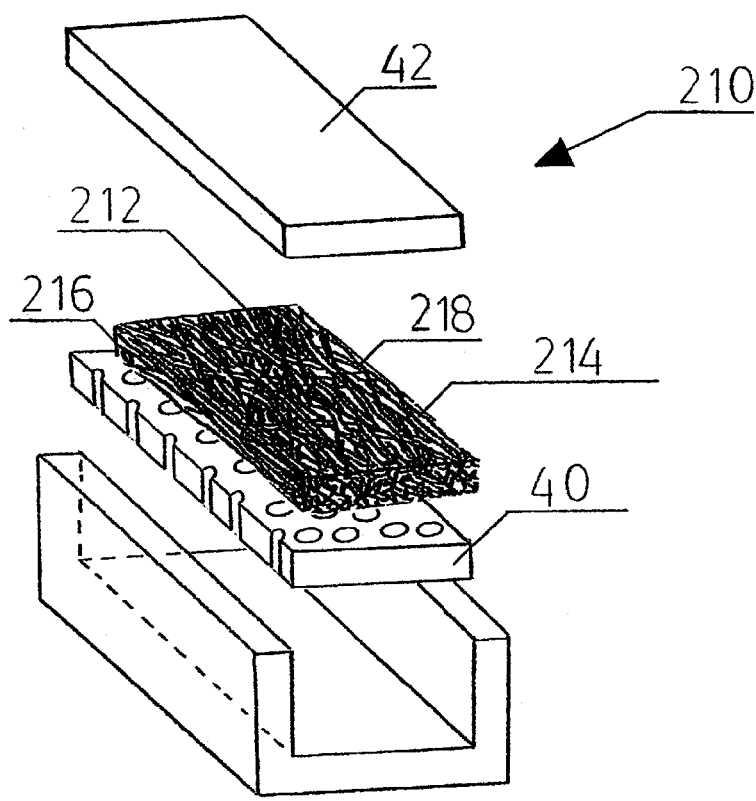
FIG. 23 is an isometric detail view showing yet another form of venting device with the individual components separated for sake of illustration.

An alternate form of surgical cast venting device is illustrated in FIG. 23. This venting device indicated generally by reference 210 is similar in its construction to the venting device 26' of FIGS. 11a and 11b except for the layer sandwiched between the lower strip 40 and the upper strip 42. In this embodiment, there is an intermediate flexible layer 212 which is arranged between and connects the inner and outer layers 40, 42. The intermediate layer 212 comprises numerous, interconnected non-woven plastic threads or thin strips 214. These threads or strips provide numerous, small irregular air passageways through which air can pass from one or more open side edges such as the longitudinal side edges 216 and 218. The layer 212 has a consistency or make-up similar to natural "Loofah", commonly used as a body sponge or body cleaning product. The layer 212 is made sufficiently thin and it contains sufficiently large air spaces between the plastic threads that each layer is flexible and is able to bend to the body contour.

Figure 9:
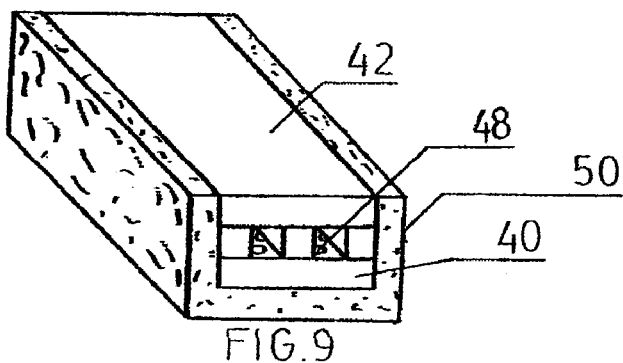
FIG. 9 is an isometric detail view illustrating the appearance of the venting device of FIG. 7 or the venting device of FIG. 8 when the components are assembled and connected together.
Figure 25:
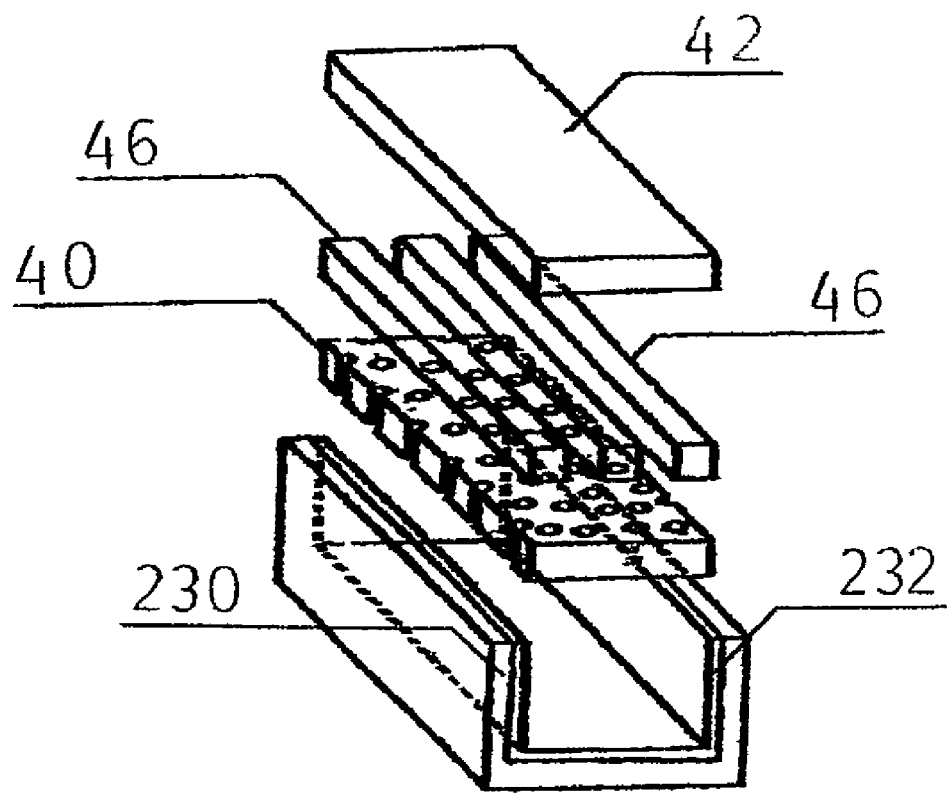
FIG. 25 is an isometric view showing the separated components of yet another form of venting device with two fabric layers.
Figure 26:
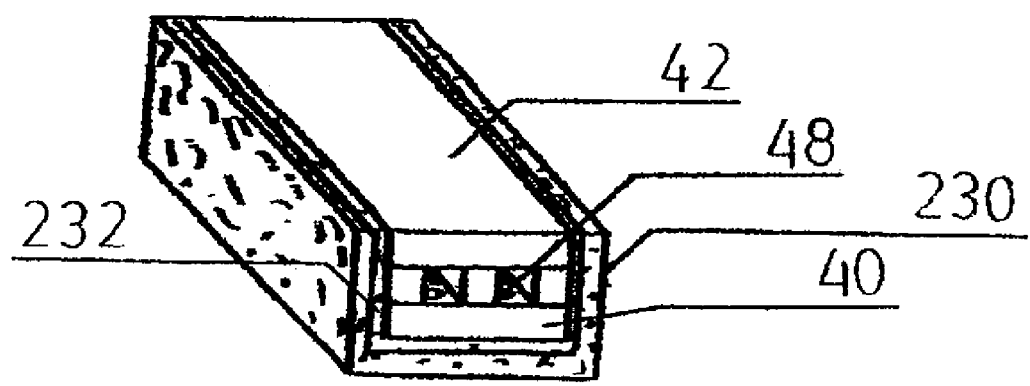
FIG. 26 is an isometric detail view illustrating the venting device of FIG. 25 when the components are assembled and connected together.

FIGS. 25 and 26 illustrate a variation of the venting device of FIGS. 7 and 9 wherein there are two layers of fabric material covering the inside surface. This venting device also includes the major components of an upper strip 42 and a lower strip 40 and extending between and connecting these two strips are a plurality of elongate spacer members 46. However instead of a single, porous fabric layer (used in the embodiment of FIGS. 7 and 9), there are two fabric layers including a porous outer layer 230 and a porous inner layer 232. In one preferred embodiment of this venting device, the outer layer is a hydrophobic fabric while the inner layer is a hydrophilic fabric such as cotton. The advantage of the hydrophobic outer layer is that it will help to keep the user's skin dry by passing any moisture or water vapor from the skin through this layer to the inner layer 232 where it will be absorbed. This is a common technique used in disposable diapers to keep a baby's skin dry.

It will be appreciated by those skilled in the art that a variety of both hydrophilic and hydrophobic fabric materials are available for use in the venting devices of the present invention provided they are skin compatible, non-toxic and non-allergenic. In addition to the natural material cotton, a variety of synthetic hydrophilic materials are usable and these include hydrophilic fabrics made of polyurethane fiber, polyamid fibers, hydrophilic polyester fibers and polypropylene fibers and polyethylene fibers. Another usable but more expensive natural fabric is that made from wool fiber.

Normally hydrophobic fibers such as nylon and polyester can be rendered hydrophilic by chemical surface treatment. Suitable chemical processes of this type are described in U.S. Pat. Nos. 4,705,831; 4,726,968; 4,743,267; 4,672,005; 4,790,907; 4,563,507; 4,806,125 and 5,154,727. These patents are incorporated herein by reference for a more complete description of a suitable chemical modification processes and synthetic hydrophilic fabrics prepared using these processes. Fabrics produced by such processes still have some hydrophobic properties and therefore they will not absorb too much fluid or become too wet.

Another suitable fabric material for use on the venting device of the invention is that taught in recent U.S. Pat. No. 6,511,927 issued Jan. 28, 2003. This patent teaches a breathable, waterproof textile laminate which includes a microporous membrane comprising a hydrophobic film having a plurality of pores of a size large enough to allow water vapor to pass therethrough but small enough to resist the passage of liquid water and a non-porous layer bonded to this microporous membrane by an adhesive. The non-porous layer comprises a hydrophilic material capable of allowing diffusion of water vapor therethrough. A fabric layer is adhered to one of the microporous membrane and the non-porous layer with a further adhesive. The specification and drawings of this U.S. patent are incorporated herein by reference.

It should be noted that the term "porous" as used in the present application to describe a fabric or material includes a fabric covered by a microporous membrane or film having pores large enough to allow water vapor to pass therethrough.

One advantage of the venting device of FIGS. 25 and 26 which has an inner layer of hydrophilic fabric is that water vapour from the skin that has passed through the outer hydrophobic fabric will usually condense on the hydrophilic material. However with the venting device of the invention, the condensed moisture will not remain but will be gradually drawn off by the circulating air which can reach the hydrophilic material through the holes in the layer 40. It will thus be appreciated that moisture and water vapor are effectively removed from the region of the skin in two ways, firstly by the hydrophobic nature of the outer layer of fabric that is in contact with the skin and secondly by the circulation of air through and over the adjacent hydrophilic material.

It is possible to use a so-called "smart bandage" with the venting devices of the present invention. These "smart bandages" are described in an article in Technology Review, May 2003 at page 73. These newly developed bandages can change color not only to warn patients and doctors that there is an infection but also to specify which bacteria is present. The so-called "smart bandage" consists of a thin sensor made of crystalline silicon and layers of porous silicone, the latter being treated with a liquid that contains probe molecules engineered to bind to fat molecules found on the surface of specific bacteria. When the bandage is placed over an infected area, bacteria from the wound move into the porous silicon and attach themselves to the probe molecules, altering the optical properties of the silicon. A doctor can illuminate the bandage with light from a handheld semiconductor laser device and the bandage luminesces in a color that indicates the kind of bacteria that is present. Such a smart bandage could be used with the venting device of FIG. 5 for example, but placing the smart bandage facing the holes 44 on the inner layer 40 near wounded areas of the skin. If there is any bacteria, it may migrate through the holes 44 and be absorbed on the smart bandage where it can be detected.

The use of a hydrophilic fabric layer 50 on the venting device can be desirable when the cast will be kept dry, which may be necessary if the covered limb or body part has an open wound, stitches or ulcers. The hydrophilic layer has the advantage of absorbing fluids seeping from the wound or ulcer.

Also a hydrophilic fabric layer 50 will allow the wearer to absorb vapors coming from a shower, for example. The absorbed moisture will dry out quickly due to the circulation of air through the venting device.

Although the various venting devices described herein can be assembled by means of double sided tape, such tape can have a limited shelf life and preferably these venting devices are assembled by means of one or more of a variety of available adhesives including ultra violet adhesives and thermal adhesives and ultrasonic welding.

It will be seen that a variety of advantages are obtained with the venting devices and venting apparatus described above. Firstly as described, it is possible to force jets of air through the venting device, such as by an air blower or dryer. Therefore the layers of the venting device can be dried faster as compared to other known venting devices and materials, even if the bottom layer is made of a hydrophilic material such as cotton and has absorbed a significant amount of water.

Another substantial advantage is that because the venting device has its own fabric layer or pad attached to its inner surface, no separate stocking or cotton layer need first be applied to the skin of a patient prior to the application of the venting device. Because the venting devices can also be made quite thin, this can result in a completed cast which is less bulky.

Also for those patients that require hydrotherapy treatment where the skin is submerged in water, the present venting device can be provided with a hydrophobic outer layer that will resist water absorption and will permit the venting device under the cast to be dried quickly.

Another advantage of the present inventing device is that it is intended for use in the form of non-overlapping coils. The result is that there is less wastage of material and less material is required to construct the venting device, keeping manufacturing costs reasonable. Also, because there is no overlapping of the materials of the venting device when applied to a user's skin, the total overall length of the wrapped venting device tends to be shorter and this in turn helps to make the drying cycle faster.

The amount of EVA material used in the present device can be reduced somewhat by the use of perforations in the upper layer 42. Indeed these perforations can be up to 4 mm in size. The removal of such material helps to reduce the weight of the venting device. In addition to these holes, it is also possible to make the upper surface of the upper layer 42 with a rough finish in order to make the applied cast more stable and less likely to shift on the surface.

Another flexible material that can be used for the layer 50 that is next to the skin is the material sold under the trademark PORON®.

If the venting devices or the venting apparatus is to be used on an animal with fur or a coat of hair, the fur or hair should be shaved off of the body part prior to application of the venting device of the invention and a cast. In this way, the venting device can be applied more securely to the body part and the flow of air to the skin of the animal will not be blocked by the fur or hair of the animal.

With respect to the thickness of the fabric layer such as the layer 50, this layer should neither be too thick nor to thin. If the fabric layer is too thin, there is a danger that holes may form in this layer and the lower layer 40 may come into contact with the skin, particularly during use of the venting device under a cast. On the other hand, if the layer 50 is too thick, this layer may unduly interfere with the circulation of air to the skin from the passageways in the venting device. In one preferred embodiment, the uncompressed thickness of the cotton layer 50 is about the same as the thickness of the lower strip 40 which, as indicated, can be about 2 mm. In some of the drawings, the cotton layer has been illustrated as being relatively thick but, in the preferred venting devices, it is no thicker than the bottom layer or bottom strip 40.

In order to attach the venting devices 26 to the tube 16 in the first embodiment, different types of adhesives can be used, for example, double sided adhesive tape which per se is known and readily available, can be used to attach the upper strip 42 to the SURGILAST® net. Alternatively, a layer of UV adhesive can be used to attach the venting devices to the tube 16. It is also possible to connect the upper strip 42 of each venting device to the tube 16 by lines of stitching using suitable thread material.

As indicated, the flexible material referred to herein as EVA that can be used to make a preferred embodiment of the venting device, is available in different densities. Preferably, if EVA material is used for the spacer members or spacer blocks, a denser form of EVA is used for these members since this will help prevent collapse of or a substantial reduction in height of the spacer members during use of the venting device under a cast. This will help to keep the air passageways open during use of the venting device.

In the case of the venting device 26 or a similar venting device wherein two elongate strips of material are used, the lower strip 40, as indicated, can be made of EVA material while the upper strip 42 can be made of a suitable material which is more elastic, such as NYPLEX®. The advantage of constructing these two strips of different material is that when the venting device is wound around a limb or body part, the upper strip 42 must generally stretch to a greater extent than the lower strip and thus it is advantageous for the upper strip to have greater elasticity.

It will be readily apparent to those skilled in the art that various modifications and changes can be made to the described and illustrated venting devices and apparatus without departing from the spirit and scope of this invention. Accordingly, all such modifications and embodiments as fall within the scope of the appended claims are intended to be part of this invention.

I claim:

1. A venting device for use under a surgical cast, brace, splint or other orthopedic device, said venting device having a length, width and opposite side edges and comprising:

two elongate strips of flexible material, the material of one of said strips being porous, said strips being spaced apart from each other and extending substantially parallel to each other both lengthwise and widthwise, said strips having inner sides which face each other and opposite outer sides;

flexible, solid spacer members arranged between said two strips and connecting said two strips together, said spacer members forming air passageways between adjacent spacer members so that air is normally free to pass along said passageways so as to permit air circulation substantially across the length and width of said venting device; and a moisture-absorbent, porous fabric layer extending in a longitudinal direction along the outer side of said one strip and covering said outer side, said fabric layer being attached to said one strip and at least partially covering said opposite side edges of the venting device that extend between said outer sides of said two elongate strips.

2. A venting device according to claim 1 wherein said one strip which is porous has numerous holes distributed evenly over said outer side, these holes extending through said one strip to its inner side.

3. A venting device according to claim 2 wherein at least said one strip is made of ethyl vinyl acetate (EVA).

4. A venting device according to claim 2 wherein said fabric layer is made of cotton.

5. A venting device according to claim 3 wherein said spacer members are made of ethyl vinyl acetate (EVA) and are elongate members each extending the length of said elongate strips.

6. A venting device according to claim 1 wherein said spacer members are elongate members and said air passageways extend longitudinally between the spacer members so that air is free to pass along the length of said strips from at least one end of said strips.

7. A venting device according to claim 1 wherein said spacer members are elongate members and extend transversely of said elongate strips, said air passageways are also transversely extending relative to the elongate strips, and air is free to pass across the width of the elongate strips from side edges of the venting device.

8. A venting device according to claim 1 wherein said spacer members comprise a plurality of relatively small, solid blocks arranged in a plurality of parallel longitudinal rows and having substantially flat top and bottom sides.

9. A venting device according to claim 1 including a hydrophobic fabric layer covering said moisture-absorbent fabric layer on an outer side thereof and attached to said moisture-absorbent fabric layer.

10. A venting apparatus for use under a surgical cast brace, splint, or similar orthopedic device, said apparatus comprising:

a porous, flexible tube of material having at least some elasticity, said tube having two opposite ends which are open and inner and outer surfaces; and a plurality of venting devices attached to said inner surface of the flexible tube and each arranged in a side edge to side edge manner relative to adjacent venting devices, said venting devices extending in a spiral manner relative to a central axis of said flexible tube, each venting device prior to attachment to said flexible tube having a length and width and comprising two elongate strips of flexible material, the material of one of said strips being porous, said strips being spaced apart from each other and extending substantially parallel to each other both lengthwise and widthwise, said strips having inner sides which face each other and opposite outer sides, said one strip of each venting device facing radially inwardly;

flexible spacer members arranged between said two strips and connecting said two strips together, said spacer members forming air passageways between adjacent spacer members so that air is normally free to pass along said passageways so as to permit air circulation substantially across the length and width of said venting device; and a moisture-absorbent, porous fabric layer extending in a longitudinal direction along the outer side of said one strip and covering said outer side, said fabric layer being attached to said one strip, wherein said venting apparatus is adapted for placement around part of a human body or animal body prior to application of said surgical cast, brace, splint or similar orthopedic device over said part of the body.

11. A venting apparatus according to claim 10 wherein said flexible tube is made of an elastic net.

12. A venting apparatus according to claim 10 wherein said venting devices are attached to the flexible tube by means of double-sided adhesive tape.

13. A venting apparatus according to claim 10 wherein said flexible tube can be twisted to reduce its diameter in order to snuggly fit around said part of the body and said one strip which is porous has numerous holes distributed evenly over said outer side thereof, these holes extending through said one strip to the inner side of said one strip.

14. A venting apparatus according to claim 10 wherein said spacer members are elongate members and extend transversely of the elongate strips, and said air passageways also extend transversely relative to the elongate strips so that air is free to pass along the width of said strips.

15. A venting apparatus according to claim 14 wherein said at least one strip of each venting device is made of ethyl vinyl acetate (EVA).

16. A venting apparatus according to claim 15 wherein said fabric layer of each venting device is made of cotton and at least covers side edges of its respective venting device that extend between outer sides of said two elongate strips.

17. A venting apparatus according to claim 10 wherein each venting device has a hydrophobic fabric layer covering said moisture-absorbent fabric layer on an outer side thereof and attached to said moisture-absorbent fabric layer.

18. A venting device according to claim 1 wherein elongate fastening devices extend along and are secured to said opposite side edges, whereby said opposite side edges can be connected to each other or to side edges of another similar venting device after said venting device or said venting devices have been wrapped around a body part of a human or animal.

19. A venting device according to claim 18 wherein a combination of said fastening devices on said opposite side edges comprises a complete zipper fastener.

20. A venting device according to claim 18 wherein a combination of said fastening devices on said opposite side edges comprises a complete multiple hook and loop type fastener.

* * * * *